(12) United States Patent
Thomas et al.

(10) Patent No.: US 12,391,867 B2
(45) Date of Patent: *Aug. 19, 2025

(54) OLEFIN SULFONATES

(71) Applicants: CHEVRON ORONITE COMPANY LLC, San Ramon, CA (US); CHEVRON U.S.A. INC., San Ramon, CA (US)

(72) Inventors: Andrew M. Thomas, El Sobrante, CA (US); Curtis B. Campbell, Hercules, CA (US); Gayani W. Pinnawala, Katy, TX (US); Varadarajan Dwarakanath, Houston, TX (US); Andrew M. Davidson, San Ramon, CA (US); Ping Wang, Fremont, CA (US)

(73) Assignees: CHEVRON ORONITE COMPANY LLC, San Ramon, CA (US); CHEVRON U.S.A. INC., San Ramon, CA (US)

( * ) Notice: Subject to any disclaimer, the term of this patent is extended or adjusted under 35 U.S.C. 154(b) by 551 days.

This patent is subject to a terminal disclaimer.

(21) Appl. No.: 17/771,984

(22) PCT Filed: Oct. 30, 2020

(86) PCT No.: PCT/US2020/058260
§ 371 (c)(1),
(2) Date: Apr. 26, 2022

(87) PCT Pub. No.: WO2021/087293
PCT Pub. Date: May 6, 2021

(65) Prior Publication Data
US 2022/0363979 A1    Nov. 17, 2022

Related U.S. Application Data

(60) Provisional application No. 62/929,025, filed on Oct. 31, 2019.

(51) Int. Cl.
C09K 8/60 (2006.01)
C09K 8/584 (2006.01)
(Continued)

(52) U.S. Cl.
CPC .............. *C09K 8/604* (2013.01); *C09K 8/584* (2013.01); *C09K 8/703* (2013.01); *C09K 23/02* (2022.01)

(58) Field of Classification Search
None
See application file for complete search history.

(56) References Cited

U.S. PATENT DOCUMENTS 2,592,428 A   4/1952 Kemp
2,814,655 A   11/1957 Langlois
(Continued)

FOREIGN PATENT DOCUMENTS

WO   2008079852 W   7/2008
WO   2008079855 A2  7/2008
(Continued)

OTHER PUBLICATIONS

Ashish Kumar et al. Diagnosing Fracture-Wellbore Connectivity Using Chemical Tracer Flowback Data URTeC 2902023 Jul. 23-25, 2018 pp. 1-10.
(Continued)

*Primary Examiner* — John J Figueroa
(74) *Attorney, Agent, or Firm* — Meunier Carlin & Curfman LLC

(57) ABSTRACT

The present disclosure is directed to surfactants (in particular olefin sulfonates), surfactant packages, compositions derived thereof, and uses thereof in hydrocarbon recovery. Methods of making olefin sulfonate surfactants are also described.

11 Claims, 4 Drawing Sheets

(51) Int. Cl.
*C09K 8/70* (2006.01)
*C09K 23/02* (2022.01)

(56) References Cited

U.S. PATENT DOCUMENTS

| | | | |
|---|---|---|---|
| 3,811,504 A | 5/1974 | Flournoy | |
| 3,811,505 A | 5/1974 | Flournoy | |
| 3,811,507 A | 5/1974 | Flournoy | |
| 3,887,634 A | 6/1975 | Hughes | |
| 3,890,239 A | 6/1975 | Dycus | |
| 4,463,806 A | 8/1984 | Hurd | |
| 4,597,879 A | 7/1986 | Morita | |
| 4,979,564 A | 12/1990 | Kalpakci | |
| 5,052,487 A | 10/1991 | Wall | |
| 5,488,148 A | 1/1996 | Weerasooriya | |
| 6,022,843 A | 2/2000 | Shanks | |
| 6,225,267 B1 | 5/2001 | Eckard | |
| 7,629,299 B2 | 12/2009 | Berger | |
| 7,770,641 B2 * | 8/2010 | Dwarakanath | C09K 8/588 166/305.1 |
| 8,183,192 B2 | 5/2012 | Sinquin | |
| 8,211,837 B2 | 7/2012 | Weerasooriya | |
| 8,293,688 B2 | 10/2012 | Campbell | |
| 8,403,044 B2 | 3/2013 | Hutchison | |
| 8,513,168 B2 | 8/2013 | Barnes | |
| 8,889,600 B2 | 11/2014 | Hutchison | |
| 8,993,798 B2 | 3/2015 | Campbell | |
| 9,284,481 B2 | 3/2016 | Barnes | |
| 9,422,469 B2 | 8/2016 | Dwarakanath | |
| 9,605,198 B2 | 3/2017 | Shong | |
| 9,617,464 B2 | 4/2017 | Dwarakanath | |
| 9,840,898 B2 | 12/2017 | Kasevich | |
| 9,890,627 B2 | 2/2018 | Kasevich | |
| 9,896,617 B2 | 2/2018 | Dwarakanath | |
| 9,902,894 B2 | 2/2018 | Dwarakanath | |
| 9,902,895 B2 | 2/2018 | Dwarakanath | |
| 9,909,053 B2 | 3/2018 | Dwarakanath | |
| 9,914,872 B2 | 3/2018 | Wehunt | |
| 9,938,473 B2 | 4/2018 | Timken | |
| 9,976,072 B2 | 5/2018 | Shong | |
| 10,184,076 B2 | 1/2019 | Barnes | |
| 10,233,382 B2 | 3/2019 | Shong | |
| 10,266,750 B2 | 4/2019 | Oghena | |
| 12,012,547 B2 * | 6/2024 | Pinnawala | C09K 8/584 |
| 2005/0199395 A1 | 9/2005 | Berger | |
| 2006/0185845 A1 | 8/2006 | Shpakoff | |
| 2006/0189486 A1 | 8/2006 | Shpakoff | |
| 2007/0191633 A1 | 8/2007 | Berger | |
| 2008/0171672 A1 | 7/2008 | Cano | |
| 2009/0044945 A1 | 2/2009 | Willberg | |
| 2009/0111717 A1 * | 4/2009 | Campbell | C09K 8/584 507/259 |
| 2009/0112014 A1 | 4/2009 | Campbell | |
| 2009/0270281 A1 | 10/2009 | Steinbrenner | |
| 2010/0004843 A1 | 1/2010 | Yu | |
| 2010/0096129 A1 | 4/2010 | Hinkel et al. | |
| 2010/0282467 A1 | 11/2010 | Hutchison | |
| 2010/0292110 A1 | 11/2010 | Pope | |
| 2010/0319920 A1 | 12/2010 | Pope | |
| 2011/0046024 A1 * | 2/2011 | Campbell | C09K 8/584 507/213 |
| 2011/0048721 A1 | 3/2011 | Pope | |
| 2011/0059872 A1 | 3/2011 | Weerasooriya | |
| 2011/0059873 A1 | 3/2011 | Weerasooriya | |
| 2011/0071057 A1 | 3/2011 | Weerasooriya | |
| 2011/0100402 A1 | 5/2011 | Soane | |
| 2011/0190174 A1 | 8/2011 | Weerasooriya | |
| 2011/0190175 A1 | 8/2011 | Steinbrenner | |
| 2011/0201531 A1 | 8/2011 | Sharma | |
| 2012/0097389 A1 * | 4/2012 | Dwarakanath | C09K 8/58 166/270.1 |
| 2013/0281327 A1 | 10/2013 | Weerasooriya | |
| 2013/0303412 A1 | 11/2013 | Luyster et al. | |
| 2014/0073541 A1 | 3/2014 | Ravikiran et al. | |
| 2014/0224490 A1 | 8/2014 | Barnes | |
| 2014/0288909 A1 | 9/2014 | Prestwood | |
| 2015/0083420 A1 | 3/2015 | Gupta | |
| 2016/0068742 A1 | 3/2016 | Solastiouk et al. | |
| 2016/0281494 A1 | 9/2016 | Shirdel | |
| 2016/0304767 A1 | 10/2016 | Barnes | |
| 2017/0037297 A1 | 2/2017 | King et al. | |
| 2017/0158947 A1 | 6/2017 | Kim | |
| 2017/0158948 A1 | 6/2017 | Kim | |
| 2017/0198202 A1 | 7/2017 | Shong | |
| 2017/0247604 A1 * | 8/2017 | Southwick | E21B 43/16 |
| 2018/0155505 A1 | 6/2018 | Kim | |
| 2018/0202273 A1 | 7/2018 | Kasevich | |
| 2018/0230788 A1 | 8/2018 | Dwarakanath | |
| 2019/0093002 A1 | 3/2019 | Doll et al. | |
| 2019/0153299 A1 | 5/2019 | Shong | |

FOREIGN PATENT DOCUMENTS

| | | |
|---|---|---|
| WO | 2009058889 W | 5/2009 |
| WO | 2011094442 A1 | 8/2011 |
| WO | 2011098493 W | 8/2011 |
| WO | 2012027757 A1 | 3/2012 |
| WO | 2014151419 W | 9/2014 |

OTHER PUBLICATIONS

Barnes, Julian R., et al.; "Application of Internal Olefin Sulfonates and Other Surfactants to EOR. Part 1: Structure—Performance Relationships for Selection at Different Reservoir Conditions"; SPE 129766, Apr. 2010, pp. 1-16.

D. B. Levitt et al., "Identification and Evaluation of High-Performance EOR Surfactants," SPE/DOE Symposium on Improved Oil Recovery, SPE 100089, pp. Apr. 22-26, 2006, Tulsa. Okla. USA 2006.

Dawarakanath et al., "Permeability Reduction Due to use of Liquid Polymers and Development of Remediation Options," SPE 179657, SPE IOR Symposium in Tulsa, 2016.

PCT International Search Report mailed on Feb. 16, 21 issued in Application No. PCT/US20/058313, filed on Oct. 30, 2020, 3 pages.

PCT Written Opinion of the International Searching Authority Report mailed on Feb. 16, 2021 issued in Application No. PCT/US20/058313, filed on Oct. 30, 2020, 6 pages.

PCT International Search Report mailed on Feb. 16, 2021 issued in Application No. PCT/US20/058260, filed on Oct. 30, 2020, 3 pages.

PCT Written Opinion of the International Searching Authority mailed on Feb. 16, 2021 issued in Application No. PCT/JS20/058260, filed on Oct. 30, 2020, 6 pages.

PCT International Search Report mailed on Feb. 16, 21 issued in Application No. PCT/US20/058329, filed on Oct. 30, 2020, 3 pages.

PCT Written Opinion of the International Searching Authority mailed on Feb. 16, 2021 issued in Application No. PCT/US20/058,329, filed on Oct. 30, 2020, 6 pages.

* cited by examiner

OLEFIN SULFONATES

TECHNICAL FIELD

This disclosure relates to olefin sulfonates, as well as compositions comprising these olefin sulfonates, and methods of making and using thereof.

BACKGROUND

Enhanced oil recovery (EOR) is an increasingly important supplemental technique for recovering oil from a reservoir after primary and secondary recovery. Many hydrocarbon reservoirs trap a significant amount of oil that is bound tightly and difficult to remove by traditional water flooding methods. EOR techniques such as Chemical Enhanced Oil Recovery (CEOR) can release oil not accessible via water flooding by utilizing surfactants that can displace the tightly bound oil.

Certain olefin sulfonates have been successfully used as surfactants in CEOR. These include alpha olefin sulfonates, isomerized olefin sulfonates, and internal olefin sulfonates, which are available as products of sulfonation process. Sulfonation is a major industrial chemical process used to make a diverse range of products. Petroleum sulfonates, in particular, are widely used as detergent additives in lubricating oils and surfactants in laundry and consumer products applications.

For large industrial applications, it can be quite costly to produce surfactants based on olefin sulfonates in large quantities. Thus, there is an ongoing need to develop cost-effective and improved methods for producing these surfactants.

SUMMARY

Described herein are surfactant packages, compositions comprising these surfactant packages, and methods of using thereof in oil and gas operations.

In some aspects, a surfactant composition is provided comprising an olefin sulfonate, wherein the olefin sulfonate is a propylene oligomer comprising one or more sulfonate groups, and wherein the propylene oligomer has an average total branching of about 3 to about 15 per molecule. In some embodiments, the propylene oligomer is a propylene tetramer, a propylene pentamer, a dimer of a propylene tetramer, a dimer of a propylene pentamer, or any combination thereof.

In some embodiments, the propylene oligomer has an average carbon number of from 9 to 50. In some embodiments, the average total branching is from about 3 to about 10. In some embodiments, the average total branching number is a sum of average total aliphatic branching and average total olefinic branching as determined by nuclear magnetic resonance (NMR) spectroscopy.

In some embodiments, the surfactant composition can further comprise water, a co-solvent (e.g., an alkanol ether, glycol ether, ethylene glycol monobutyl ether (EGBE), triethylene glycol butyl ether (TGBE)), residual base (e.g., NaOH), unreacted starting materials and/or byproducts remaining from the synthesis of the olefin sulfonate, or any combination thereof.

In some aspects, a concentrated surfactant composition is provided comprising an olefin sulfonate, wherein the olefin sulfonate is a propylene oligomer having an average total branching of about 3 to about 15, and wherein the olefin sulfonate is present in about 10 wt. % to about 95 wt. % based on the total weight of the concentrated surfactant composition.

In other aspects, a process for providing a surfactant is disclosed, the process comprising: reacting a propylene oligomer with $SO_3$ in the presence of air to form an olefin sulfonic acid, wherein the propylene oligomer is a propylene tetramer, propylene pentamer, dimer of a propylene tetramer, dimer of a propylene pentamer, or any combination thereof, and wherein the propylene oligomer has an average total branching of about 3 to about 15 per molecule; and neutralizing or hydrolyzing the sulfonic acid with a base to form a propylene oligomer sulfonate. In some embodiments, the base has a monovalent cation. In some embodiments, the monovalent cation comprises sodium, lithium, potassium, ammonium, substituted ammonium, or any combination thereof. In some embodiments, the base comprises a carbonate, a hydroxide, a bicarbonate, an ammonium, an amine, or any combination thereof. In some embodiments, the base comprises NaOH. In some embodiments, the propylene oligomer and $SO_3$ are reacted in a falling film reactor. In some embodiments, the temperature of the reactor ranges from 0 to 80° C. In some embodiments, the concentration of $SO_3$ in the reactor ranges from about 0.1 wt. % to about 10 wt. % based on the total weight of all reactants combined in the reactor. In some embodiments, the average total branching is a sum of average total aliphatic branching and average total olefinic branching as determined by nuclear magnetic resonance (NMR) spectroscopy.

Also provided are aqueous surfactant compositions for use in oil and gas operations. These surfactant compositions can comprise water, an olefin sulfonate described herein, and one or more additional components chosen from one or more co-surfactants, a viscosity-modifying polymer, or any combination thereof. The one or more co-surfactants can comprise an anionic surfactant, a non-ionic surfactant, a cationic surfactant, a zwitterionic surfactant, or any combination thereof. The olefin sulfonate can have a concentration within the surfactant composition of from 0.05% to 5% by weight, based on the total weight of the surfactant composition. The one or more co-surfactants can have a concentration within the surfactant composition of from 0.05% to 5% by weight, based on the total weight of the surfactant composition.

The water can comprise sea water, brackish water, fresh water, flowback or produced water, wastewater, river water, lake or pond water, aquifer water, brine, or any combination thereof. In certain examples, the water can comprise hard water or hard brine. In some embodiments, the water can comprise at least 10 ppm at least 100 ppm, at least 500 ppm, at least 1,000 ppm, at least 5,000 ppm, or at least 10,000 ppm of divalent metal ions chosen from $Ca^{2+}$, $Mg^{2+}$, $Sr^{2+}$, $Ba^{2+}$, or any combination thereof. In certain embodiments, the water can comprise from 100 ppm to 25,000 ppm of divalent metal ions chosen from $Ca^{2+}$, $Mg^{2+}$, $Sr^{2+}$, $Ba^{2+}$, or any combination thereof.

In some examples, the one or more co-surfactants can comprise an anionic surfactant, such as a sulfonate, a disulfonate, a sulfate, a disulfate, a sulfosuccinate, a disulfosuccinate, a carboxylate, a dicarboxylate, or any combination thereof. In certain examples, the anionic surfactant can comprise one of the following: a branched or unbranched C6-C32:PO(0-65):EO(0-100)-carboxylate; a C8-C30 alkyl benzene sulfonate (ABS); a sulfosuccinate surfactant; a surfactant defined by the formula below

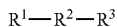

wherein $R^1$ comprises a branched or unbranched, saturated or unsaturated, cyclic or non-cyclic, hydrophobic carbon chain having 6-32 carbon atoms and an oxygen atom linking $R^1$ and $R^2$; $R^2$ comprises an alkoxylated chain comprising at least one oxide group selected from the group consisting of ethylene oxide, propylene oxide, butylene oxide, or any combination thereof; and $R^3$ comprises a branched or unbranched hydrocarbon chain comprising 2-12 carbon atoms and from 2 to 5 carboxylate groups; or a surfactant defined by the formula below

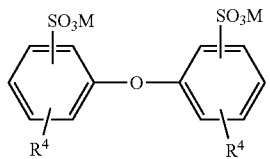

wherein $R^4$ is, independently for each occurrence, a branched or unbranched, saturated or unsaturated, cyclic or non-cyclic, hydrophobic carbon chain having 6-32 carbon atoms; and M represents a counterion.

In some examples, the one or more co-surfactants can comprise a non-ionic surfactant. In certain examples, the non-ionic surfactant can comprise a branched or unbranched C6-C32:PO(0-65):EO(0-100), such as a branched or unbranched C6-C30:PO(30-40):EO(25-35), a branched or unbranched C6-C12:PO(30-40):EO(25-35), or a branched or unbranched C6-C30:EO(8-30). In certain examples, the non-ionic surfactant can have a hydrophilic-lipophilic balance of greater than 10.

In some embodiments, the surfactant composition can further comprise a co-solvent, a friction reducer, a gelling agent, a crosslinker, a breaker, a pH adjusting agent, a non-emulsifier agent, an iron control agent, a corrosion inhibitor, a scale inhibitor, a biocide, a clay stabilizing agent, a chelating agent, a proppant, a wettability alteration chemical, or any combination thereof.

In some embodiments, the surfactant composition can further comprise an acid, a base, or any combination thereof. In some embodiments, the surfactant composition can further comprise a borate-acid buffer.

Also provided are methods of using the olefin surfactants described herein in oil and gas operations. The oil and gas operation can comprise for example, an enhanced oil recovery (EOR) operation (e.g., an improved oil recovery (IOR) operation, a surfactant (S) flooding operation, an alkaline-surfactant (AS) flooding operation, a surfactant-polymer (SP) flooding operation, a alkaline-surfactant-polymer (ASP) flooding operation, a conformance control operation, or any combination thereof), a hydraulic fracturing operation, a wellbore clean-up operation, a stimulation operation, or any combination thereof. In certain examples, the surfactant compositions described herein can be used as an injection fluid, as a component of an injection fluid, as a hydraulic fracturing fluid, or as a component of a hydraulic fracturing fluid.

For example, provided herein methods of treating a subterranean formation that comprise introducing an aqueous fluid comprising water and a surfactant package through a wellbore into the subterranean formation. The surfactant package can comprise an olefin sulfonate described herein.

In some embodiments, the surfactant package comprises a primary surfactant and one or more secondary surfactants. The primary surfactant can comprise from 10% to 90% by weight of the surfactant package. The one or more secondary surfactants can comprise from 10% to 90% by weight of the surfactant package. The primary surfactant, the one or more secondary surfactants, or any combination thereof can comprise an olefin sulfonate described herein.

In some embodiments, the primary surfactant can comprise the olefin sulfonate described herein. The one or more secondary surfactants can comprise an anionic surfactant, a non-ionic surfactant, a cationic surfactant, a zwitterionic surfactant, an amphoteric surfactant, or any combination thereof. In some examples, the one or more secondary surfactants can comprise an anionic surfactant, such as a sulfonate, a disulfonate, a sulfate, a disulfate, a sulfosuccinate, a disulfosuccinate, a carboxylate, a dicarboxylate, or any combination thereof. In certain examples, the anionic surfactant can comprise one of the following: a branched or unbranched C6-C32:PO(0-65):EO(0-100)-carboxylate; a C8-C30 alkyl benzene sulfonate (ABS); a sulfosuccinate surfactant; a surfactant defined by the formula below

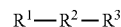

wherein $R^1$ comprises a branched or unbranched, saturated or unsaturated, cyclic or non-cyclic, hydrophobic carbon chain having 6-32 carbon atoms and an oxygen atom linking $R^1$ and $R^2$; $R^2$ comprises an alkoxylated chain comprising at least one oxide group selected from the group consisting of ethylene oxide, propylene oxide, butylene oxide, or any combination thereof; and $R^3$ comprises a branched or unbranched hydrocarbon chain comprising 2-12 carbon atoms and from 2 to 5 carboxylate groups; or a surfactant defined by the formula below

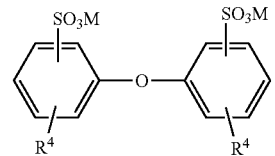

wherein $R^4$ is, independently for each occurrence, a branched or unbranched, saturated or unsaturated, cyclic or non-cyclic, hydrophobic carbon chain having 6-32 carbon atoms; and M represents a counterion.

In some examples, the one or more secondary surfactants can comprise a non-ionic surfactant. In certain examples, the non-ionic surfactant can comprise a branched or unbranched C6-C32:PO(0-65):EO(0-100), such as a branched or unbranched C6-C30:PO(30-40):EO(25-35), a branched or unbranched C6-C12:PO(30-40):EO(25-35), or a branched or unbranched C6-C30:EO(8-30). In certain examples, the non-ionic surfactant can have a hydrophilic-lipophilic balance of greater than 10.

In some embodiments, the one or more secondary surfactants can comprise the olefin sulfonate described herein.

In certain embodiments, the one or more secondary surfactants comprise the olefin sulfonate and one or more additional surfactants. The primary surfactant can comprise an anionic surfactant, a non-ionic surfactant, a cationic surfactant, a zwitterionic surfactant, an amphoteric surfactant, or any combination thereof. In some examples, the primary surfactant can comprise an anionic surfactant, such as a sulfonate, a disulfonate, a sulfate, a disulfate, a sulfosuccinate, a disulfosuccinate, a carboxylate, a dicarboxylate, or any combination thereof. In certain examples, the anionic surfactant can comprise one of the following: a branched or unbranched C6-C32:PO(0-65):EO(0-100)-carboxylate; a C8-C30 alkyl benzene sulfonate (ABS); a sulfosuccinate surfactant; a surfactant defined by the formula below

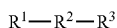

wherein $R^1$ comprises a branched or unbranched, saturated or unsaturated, cyclic or non-cyclic, hydrophobic carbon chain having 6-32 carbon atoms and an oxygen atom linking $R^1$ and $R^2$; $R^2$ comprises an alkoxylated chain comprising at least one oxide group selected from the group consisting of ethylene oxide, propylene oxide, butylene oxide, or any combination thereof; and $R^3$ comprises a branched or unbranched hydrocarbon chain comprising 2-12 carbon atoms and from 2 to 5 carboxylate groups; or a surfactant defined by the formula below

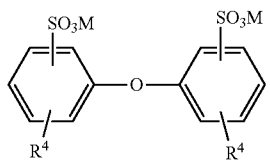

wherein $R^4$ is, independently for each occurrence, a branched or unbranched, saturated or unsaturated, cyclic or non-cyclic, hydrophobic carbon chain having 6-32 carbon atoms; and M represents a counterion.

In some examples, the primary surfactant can comprise a non-ionic surfactant. In certain examples, the non-ionic surfactant can comprise a branched or unbranched C6-C32:PO(0-65):EO(0-100), such as a branched or unbranched C6-C30:PO(30-40):EO(25-35), a branched or unbranched C6-C12:PO(30-40):EO(25-35), or a branched or unbranched C6-C30:EO(8-30). In certain examples, the non-ionic surfactant can have a hydrophilic-lipophilic balance of greater than 10.

In some embodiments, the methods of treating the subterranean formation can comprise a stimulation operation. For example, the method can comprise (a) injecting the aqueous fluid through the wellbore into the subterranean formation; (b) allowing the aqueous fluid to imbibe into a rock matrix of the subterranean formation for a period of time; and (c) producing fluids from the subterranean formation through the wellbore.

In some embodiments, the methods of treating the subterranean formation can comprise a fracturing operation. For example, the method can comprise injecting the aqueous fluid into the subterranean formation through the wellbore at a sufficient pressure to create or extend at least one fracture in a rock matrix of the subterranean formation in fluid communication with the wellbore.

In some embodiments, the methods of treating the subterranean formation can comprise an EOR operation. For example, the wellbore can comprise an injection wellbore, and the method can comprise a method for hydrocarbon recovery that comprises (a) injecting the aqueous fluid through the injection wellbore into the subterranean formation; and (b) producing fluids from a production wellbore spaced apart from the injection wellbore a predetermined distance and in fluid communication with the subterranean formation. The injection of the aqueous fluid can increase the flow of hydrocarbons to the production well.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
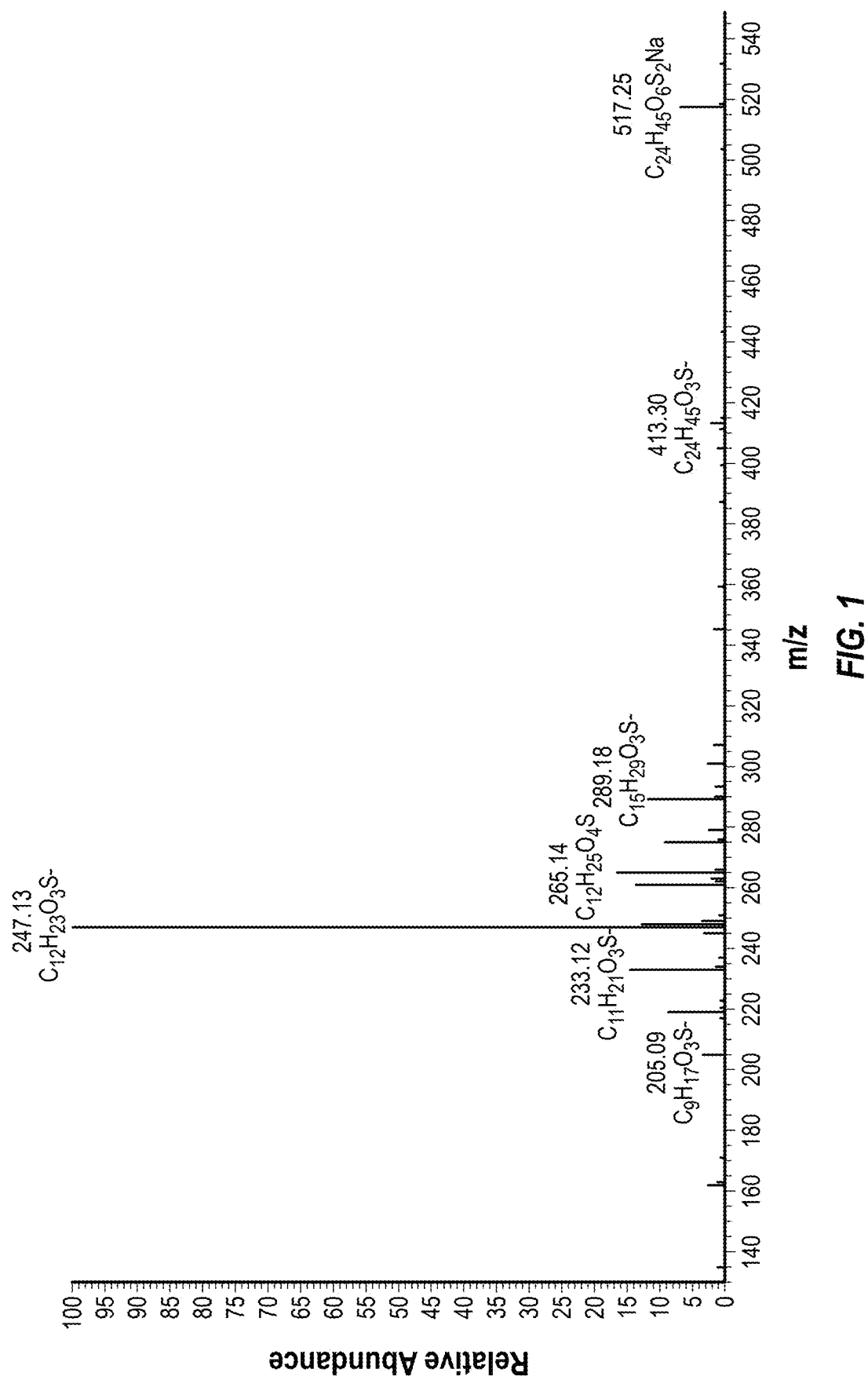
FIG. 1 is a mass spectrum of an internal olefin sulfonate sample as described in Example 2.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%. Furthermore, a range may be construed to include the start and the end of the range. For example, a range of 10% to 20% (i.e., range of 10%-20%) can includes 10% and also includes 20%, and includes percentages in between 10% and 20%, unless explicitly stated otherwise herein.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

The term "hydrocarbon" refers to a compound containing only carbon and hydrogen atoms.

The term "olefin" refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono", "di", "tri", etc. within the name of the olefin.

An "olefin oligomer" is an oligomer made from oligomerization of olefin monomers. For example, a "propylene oligomer" is made from the oligomerization of nominally propylene monomers. Examples of propylene oligomers include propylene tetramer and propylene pentamer. These terms also can be used generically herein to described propylene homo-oligomers, propylene co-oligomers, salts of propylene oligomers, derivatives of propylene oligomers, and the like.

"Hydrocarbon-bearing formation" or simply "formation" refers to the rock matrix in which a wellbore may be drilled. For example, a formation refers to a body of rock that is sufficiently distinctive and continuous such that it can be mapped. It should be appreciated that while the term "formation" generally refers to geologic formations of interest, that the term "formation," as used herein, may, in some instances, include any geologic points or volumes of interest (such as a survey area).

"Unconventional formation" is a subterranean hydrocarbon-bearing formation that generally requires intervention in order to recover hydrocarbons from the reservoir at economic flow rates or volumes. For example, an unconventional formation includes reservoirs having an unconventional microstructure in which fractures are used to recover hydrocarbons from the reservoir at sufficient flow rates or volumes (e.g., an unconventional reservoir generally needs to be fractured under pressure or have naturally occurring fractures in order to recover hydrocarbons from the reservoir at sufficient flow rates or volumes).

In some embodiments, the unconventional formation can include a reservoir having a permeability of less than 25 millidarcy (mD) (e.g., 20 mD or less, 15 mD or less, 10 mD or less, 5 mD or less, 1 mD or less, 0.5 mD or less, 0.1 mD or less, 0.05 mD or less, 0.01 mD or less, 0.005 mD or less, 0.001 mD or less, 0.0005 mD or less, 0.0001 mD or less, 0.00005 mD or less, 0.00001 mD or less, 0.000005 mD or less, 0.000001 mD or less, or less). In some embodiments, the unconventional formation can include a reservoir having a permeability of at least 0.000001 mD (e.g., at least 0.000005 mD, at least 0.00001 mD, 0.00005 mD, at least 0.0001 mD, 0.0005 mD, 0.001 mD, at least 0.005 mD, at least 0.01 mD, at least 0.05 mD, at least 0.1 mD, at least 0.5 mD, at least 1 mD, at least 5 mD, at least 10 mD, at least 15 mD, or at least 20 mD).

The unconventional formation can include a reservoir having a permeability ranging from any of the minimum values described above to any of the maximum values described above. For example, in some embodiments, the unconventional formation can include a reservoir having a permeability of from 0.000001 mD to 25 mD (e.g., from 0.001 mD to 25 mD, from 0.001 mD to 10 mD, from 0.01 mD to 10 mD, from 0.1 mD to 10 mD, from 0.001 mD to 5 mD, from 0.01 mD to 5 mD, or from 0.1 mD to 5 mD).

The formation may include faults, fractures (e.g., naturally occurring fractures, fractures created through hydraulic fracturing, etc.), geobodies, overburdens, underburdens, horizons, salts, salt welds, etc. The formation may be onshore, offshore (e.g., shallow water, deep water, etc.), etc. Furthermore, the formation may include hydrocarbons, such as liquid hydrocarbons (also known as oil or petroleum), gas hydrocarbons, any combination of liquid hydrocarbons and gas hydrocarbons (e.g. including gas condensate), etc.

The formation, the hydrocarbons, or both may also include non-hydrocarbon items, such as pore space, connate water, brine, fluids from enhanced oil recovery, etc. The formation may also be divided up into one or more hydrocarbon zones, and hydrocarbons can be produced from each desired hydrocarbon zone.

The term formation may be used synonymously with the term reservoir. For example, in some embodiments, the reservoir may be, but is not limited to, a shale reservoir, a carbonate reservoir, a tight sandstone reservoir, a tight siltstone reservoir, a gas hydrate reservoir, a coalbed methane reservoir, etc. Indeed, the terms "formation," "reservoir," "hydrocarbon," and the like are not limited to any description or configuration described herein.

"Wellbore" refers to a continuous hole for use in hydrocarbon recovery, including any openhole or uncased portion of the wellbore. For example, a wellbore may be a cylindrical hole drilled into the formation such that the wellbore is surrounded by the formation, including rocks, sands, sediments, etc. A wellbore may be used for injection. A wellbore may be used for production. A wellbore may be used for hydraulic fracturing of the formation. A wellbore even may be used for multiple purposes, such as injection and production. The wellbore may have vertical, inclined, horizontal, or any combination of trajectories. For example, the wellbore may be a vertical wellbore, a horizontal wellbore, a multilateral wellbore, or slanted wellbore. The wellbore may include a "build section." "Build section" refers to practically any section of a wellbore where the deviation is changing. As an example, the deviation is changing when the wellbore is curving. The wellbore may include a plurality of components, such as, but not limited to, a casing, a liner, a tubing string, a heating element, a sensor, a packer, a screen, a gravel pack, etc. The wellbore may also include equipment to control fluid flow into the wellbore, control fluid flow out of the wellbore, or any combination thereof. For example, each wellbore may include a wellhead, a BOP, chokes, valves, or other control devices. These control devices may be located on the surface, under the surface (e.g., downhole in the wellbore), or any combination thereof. The wellbore may also include at least one artificial lift device, such as, but not limited to, an electrical submersible pump (ESP) or gas lift. Some non-limiting examples of wellbores may be found in U.S. Patent Application Publication No. 2014/0288909 and U.S. Patent Application Publication No. 2016/0281494A1, each of which is incorporated by reference in its entirety. The term wellbore is not limited to any description or configuration described herein. The term wellbore may be used synonymously with the terms borehole or well.

"Single-phase liquid or fluid," as used herein, refers to a fluid which only has a single-phase, i.e. only a water phase. A single-phase fluid is not an emulsion. A single-phase fluid is in a thermodynamically stable state such that it does not macroscopically separate into distinct layers or precipitate out solid particles. In some embodiments, the single-phase liquid comprises a single-phase liquid surfactant package including one or more anionic and/or non-ionic surfactants.

"Aqueous stable," as used herein, refers to a solution whose soluble components remain dissolved and is a single phase as opposed to precipitating as particulates or phase separating into 2 or more phases. As such, aqueous stable solutions are clear and transparent statically and when agitated. Conversely, solutions may be described as "aqueous unstable" when components precipitate from solution as particulates or phase separates into 2 or more phases. The aqueous stability of solutions can be assessed by evaluating whether the Tyndall Effect (light scattering by suspended particulates) is observed when monochromatic light is directed through the solution. If a sample exhibits the Tyndall effect, the solution may be characterized as "aqueous unstable." Conversely, if a sample does not exhibit the Tyndall effect, the solution may be characterized as "aqueous stable."

"Slickwater," as used herein, refers to water-based injection fluid comprising a friction reducer which is typically pumped at high rates to fracture a reservoir. Optionally when employing slickwater, smaller sized proppant particles (e.g., 40/70 or 50/140 mesh size) are used due to the fluid having a relatively low viscosity (and therefore a diminished ability to transport sizable proppants relative to more viscous fluids). In some embodiments, proppants are added to some stages of completion/stimulation during production of an unconventional reservoir. In some embodiments, slickwater is injected with a small quantity of proppant.

"Friction reducer," as used herein, refers to a chemical additive that alters fluid rheological properties to reduce friction created within the fluid as it flows through small-diameter tubulars or similar restrictions (e.g., valves, pumps). Generally polymers, or similar friction reducing agents, add viscosity to the fluid, which reduces the turbulence induced as the fluid flows. Reductions in fluid friction of greater than 50% are possible depending on the friction reducer utilized, which allows the injection fluid to be injected into a wellbore at a much higher injection rate (e.g., between 60 to 100 barrels per minute) and also lower pumping pressure during proppant injection.

"Injection fluid," as used herein, refers to any fluid which is injected into a reservoir via a well. The injection fluid may include one or more of an acid, a polymer, a friction reducer, a gelling agent, a crosslinker, a scale inhibitor, a breaker, a pH adjusting agent, a non-emulsifier agent, an iron control agent, a corrosion inhibitor, a biocide, a clay stabilizing agent, a proppant, a wettability alteration chemical, a co-solvent (e.g., a C1-C5 alcohol, or an alkoxylated C1-C5 alcohol), or any combination thereof, to increase the efficacy of the injection fluid. In some embodiments, the injection fluid can be a low-particle size injection fluid as described below.

"Low particle size injection fluid" refers to an injection fluid having a maximum particle size of less than 0.1 micrometers in diameter in particle size distribution measurements performed at a temperature and salinity of the unconventional formation for which injection is to occur. For example, the low particle size injection fluid can be formed by mixing an aqueous-based injection fluid with a surfactant package described herein. Prior to being dosed with the surfactant package to form the low particle size injection fluid, the aqueous-based injection fluid may have been used as the injection fluid.

"Fracturing" is one way that hydrocarbons may be recovered (sometimes referred to as produced) from the formation. For example, hydraulic fracturing may entail preparing a fracturing fluid and injecting that fracturing fluid into the wellbore at a sufficient rate and pressure to open existing fractures and/or create fractures in the formation. The fractures permit hydrocarbons to flow more freely into the wellbore. In the hydraulic fracturing process, the fracturing fluid may be prepared on-site to include at least proppants. The proppants, such as sand or other particles, are meant to hold the fractures open so that hydrocarbons can more easily flow to the wellbore. The fracturing fluid and the proppants may be blended together using at least one blender. The fracturing fluid may also include other components in addition to the proppants.

The wellbore and the formation proximate to the wellbore are in fluid communication (e.g., via perforations), and the fracturing fluid with the proppants is injected into the wellbore through a wellhead of the wellbore using at least one pump (oftentimes called a fracturing pump). The fracturing fluid with the proppants is injected at a sufficient rate and pressure to open existing fractures and/or create fractures in the subsurface volume of interest. As fractures become sufficiently wide to allow proppants to flow into those fractures, proppants in the fracturing fluid are deposited in those fractures during injection of the fracturing fluid. After the hydraulic fracturing process is completed, the fracturing fluid is removed by flowing or pumping it back out of the wellbore so that the fracturing fluid does not block the flow of hydrocarbons to the wellbore. The hydrocarbons will typically enter the same wellbore from the formation and go up to the surface for further processing.

The equipment to be used in preparing and injecting the fracturing fluid may be dependent on the components of the fracturing fluid, the proppants, the wellbore, the formation, etc. However, for simplicity, the term "fracturing apparatus" is meant to represent any tank(s), mixer(s), blender(s), pump(s), manifold(s), line(s), valve(s), fluid(s), fracturing fluid component(s), proppants, and other equipment and non-equipment items related to preparing the fracturing fluid and injecting the fracturing fluid.

Other hydrocarbon recovery processes may also be utilized to recover the hydrocarbons. Furthermore, those of ordinary skill in the art will appreciate that one hydrocarbon recovery process may also be used in combination with at least one other recovery process or subsequent to at least one other recovery process. Moreover, hydrocarbon recovery processes may also include stimulation or other treatments.

"Fracturing fluid," as used herein, refers to an injection fluid that is injected into the well under pressure in order to cause fracturing within a portion of the reservoir.

The term "interfacial tension" or "IFT" as used herein refers to the surface tension between test oil and water of different salinities containing a surfactant formulation at different concentrations. Typically, interfacial tensions are measured using a spinning drop tensiometer or calculated from phase behavior experiments.

The term "proximate" is defined as "near". If item A is proximate to item B, then item A is near item B. For example, in some embodiments, item A may be in contact with item B. For example, in some embodiments, there may be at least one barrier between item A and item B such that item A and item B are near each other, but not in contact with each other. The barrier may be a fluid barrier, a non-fluid barrier (e.g., a structural barrier), or any combination thereof. Both scenarios are contemplated within the meaning of the term "proximate."

The term "contacting" as used herein, refers to materials or compounds being sufficiently close in proximity to react or interact. For example, in methods of contacting an unrefined petroleum material, a hydrocarbon-bearing formation, and/or a wellbore, the term "contacting" can include placing a compound (e.g., a surfactant) or an aqueous composition (e.g., chemical, surfactant or polymer) within a hydrocarbon-bearing formation using any suitable manner known in the art (e.g., pumping, injecting, pouring, releasing, displacing, spotting or circulating the chemical into a well, wellbore or hydrocarbon-bearing formation).

The terms "unrefined petroleum" and "crude oil" are used interchangeably and in keeping with the plain ordinary usage of those terms. "Unrefined petroleum" and "crude oil" may be found in a variety of petroleum reservoirs (also referred to herein as a "reservoir," "oil field deposit" "deposit" and the like) and in a variety of forms including oleaginous materials, oil shales (i.e., organic-rich fine-grained sedimentary rock), tar sands, light oil deposits, heavy oil deposits, and the like. "Crude oils" or "unrefined petroleums" generally refer to a mixture of naturally occurring hydrocarbons that may be refined into diesel, gasoline, heating oil, jet fuel, kerosene, and other products called fuels or petrochemicals. Crude oils or unrefined petroleums are named according to their contents and origins, and are classified according to their per unit weight (specific gravity). Heavier crudes generally yield more heat upon burning, but have lower gravity as defined by the American Petroleum Institute (API) (i.e., API gravity) and market price in comparison to light (or sweet) crude oils. Crude oil may also be characterized by its Equivalent Alkane Carbon Number (EACN). The term "API gravity" refers to the measure of how heavy or light a petroleum liquid is compared to water. If an oil's API gravity is greater than 10, it is lighter and floats on water, whereas if it is less than 10, it is heavier and sinks. API gravity is thus an inverse measure of the relative density of a petroleum liquid and the density of water. API gravity may also be used to compare the relative densities of petroleum liquids. For example, if one petroleum liquid floats on another and is therefore less dense, it has a greater API gravity.

Crude oils vary widely in appearance and viscosity from field to field. They range in color, odor, and in the properties they contain. While all crude oils are mostly hydrocarbons, the differences in properties, especially the variation in molecular structure, determine whether a crude oil is more or less easy to produce, pipeline, and refine. The variations may even influence its suitability for certain products and the quality of those products. Crude oils are roughly classified into three groups, according to the nature of the hydrocarbons they contain. (i) Paraffin-based crude oils contain higher molecular weight paraffins, which are solid at room temperature, but little or no asphaltic (bituminous) matter. They can produce high-grade lubricating oils. (ii) Asphaltene based crude oils contain large proportions of asphaltic matter, and little or no paraffin. Some are predominantly naphthenes and so yield lubricating oils that are sensitive to temperature changes than the paraffin-based crudes. (iii) Mixed based crude oils contain both paraffin and naphthenes, as well as aromatic hydrocarbons. Most crude oils fit this latter category.

"Reactive" crude oil, as referred to herein, is crude oil containing natural organic acidic components (also referred to herein as unrefined petroleum acid) or their precursors such as esters or lactones. These reactive crude oils can generate soaps (carboxylates) when reacted with alkali. More terms used interchangeably for crude oil throughout this disclosure are hydrocarbons, hydrocarbon material, or active petroleum material. An "oil bank" or "oil cut" as referred to herein, is the crude oil that does not contain the injected chemicals and is pushed by the injected fluid during an enhanced oil recovery process. A "nonactive oil," as used herein, refers to an oil that is not substantially reactive or crude oil not containing significant amounts of natural organic acidic components or their precursors such as esters or lactones such that significant amounts of soaps are generated when reacted with alkali. A nonactive oil as referred to herein includes oils having an acid number of less than 0.5 mg KOH/g of oil.

"Unrefined petroleum acids" as referred to herein are carboxylic acids contained in active petroleum material (reactive crude oil). The unrefined petroleum acids contain $C_{11}$-$C_{20}$ alkyl chains, including napthenic acid mixtures. The recovery of such "reactive" oils may be performed using alkali (e.g., NaOH or $Na_2CO_3$) in a surfactant composition. The alkali reacts with the acid in the reactive oil to form soap in situ. These in situ generated soaps serve as a source of surfactants minimizing the levels of added surfactants, thus enabling efficient oil recovery from the reservoir.

The term "polymer" refers to a molecule having a structure that essentially includes the multiple repetitions of units derived, actually or conceptually, from molecules of low relative molecular mass. In some embodiments, the polymer is an oligomer.

The term "productivity" as applied to a petroleum or oil well refers to the capacity of a well to produce hydrocarbons (e.g., unrefined petroleum); that is, the ratio of the hydrocarbon flow rate to the pressure drop, where the pressure drop is the difference between the average reservoir pressure and the flowing bottom hole well pressure (i.e., flow per unit of driving force).

The term "oil solubilization ratio" is defined as the volume of oil solubilized divided by the volume of surfactant in microemulsion. All the surfactant is presumed to be in the microemulsion phase. The oil solubilization ratio is applied for Winsor type I and type III behavior. The volume of oil solubilized is found by reading the change between initial aqueous level and excess oil (top) interface level. The oil solubilization ratio is calculated as follows:

$$\sigma_o = \frac{V_o}{V_s}$$

where $\sigma_o$ is the oil solubilization ratio, $V_o$ is the volume of oil solubilized, and $V_s$ is the volume of surfactant.

The term "water solubilization ratio" is defined as the volume of water solubilized divided by the volume of surfactant in microemulsion. All the surfactant is presumed to be in the microemulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{V_s}$$

where $\sigma_w$ is the water solubilization ratio, $V_w$ is the volume of oil solubilized, and $V_s$ is the volume of surfactant.

The optimum solubilization ratio occurs where the oil and water solubilization ratios are equal. The coarse nature of phase behavior screening often does not include a data point at optimum, so the solubilization ratio curves are drawn for the oil and water solubilization ratio data and the intersection of these two curves is defined as the optimum. The following is true for the optimum solubilization ratio:

$$\sigma_o = \sigma_w = \sigma^*$$

where $\sigma^*$ is the optimum solubilization ratio.

The term "solubility" or "solubilization" in general refers to the property of a solute, which can be a solid, liquid or gas, to dissolve in a solid, liquid or gaseous solvent thereby forming a homogenous solution of the solute in the solvent. Solubility occurs under dynamic equilibrium, which means that solubility results from the simultaneous and opposing processes of dissolution and phase joining (e.g., precipitation of solids). The solubility equilibrium occurs when the two processes proceed at a constant rate. The solubility of a given solute in a given solvent typically depends on temperature. For many solids dissolved in liquid water, the solubility increases with temperature. In liquid water at high temperatures, the solubility of ionic solutes tends to decrease due to the change of properties and structure of liquid water. In more particular, solubility and solubilization as referred to herein is the property of oil to dissolve in water and vice versa.

"Viscosity" refers to a fluid's internal resistance to flow or being deformed by shear or tensile stress. In other words, viscosity may be defined as thickness or internal friction of a liquid. Thus, water is "thin", having a lower viscosity, while oil is "thick", having a higher viscosity. More generally, the less viscous a fluid is, the greater its ease of fluidity.

The term "salinity" as used herein, refers to concentration of salt dissolved in an aqueous phases. Examples for such salts are without limitation, sodium chloride, magnesium and calcium sulfates, and bicarbonates. In more particular, the term salinity as it pertains to the present invention refers to the concentration of salts in brine and surfactant solutions.

The term "co-solvent," as used herein, refers to a compound having the ability to increase the solubility of a solute (e.g., a surfactant as disclosed herein) in the presence of an unrefined petroleum acid. In some embodiments, the co-solvents provided herein have a hydrophobic portion (alkyl or aryl chain), a hydrophilic portion (e.g., an alcohol) and optionally an alkoxy portion. Co-solvents as provided herein include alcohols (e.g., $C_1$-$C_6$ alcohols, $C_1$-$C_6$ diols), alkoxy alcohols (e.g., $C_1$-$C_6$ alkoxy alcohols, $C_1$-$C_6$ alkoxy diols, and phenyl alkoxy alcohols), glycol ether, glycol and glycerol. The term "alcohol" is used according to its ordinary meaning and refers to an organic compound containing an —OH groups attached to a carbon atom. The term "diol" is used according to its ordinary meaning and refers to an organic compound containing two —OH groups attached to two different carbon atoms. The term "alkoxy alcohol" is used according to its ordinary meaning and refers to an organic compound containing an alkoxy linker attached to a —OH group The phrase "point of zero charge," as used herein, refers to the pH at which the surface charge (i.e., zeta potential) of a solid material, such as the rock matrix in a subterranean reservoir, is zero.

The phrase "surfactant package," as used herein, refers to one or more surfactants which are present in a composition.
Olefin Sulfonates and Methods for Making the Same This disclosure describes surfactant compositions comprising olefin sulfonates (e.g., internal olefin sulfonates) that are particularly useful in oil and gas operations, including hydrocarbon recovery. The olefin sulfonates can allow for greater recovery of hydrocarbons when used in techniques such as surfactant flooding, wettability alteration, hydraulic fracturing, and the like. This disclosure describes methods for making olefin sulfonates and for using the same in hydrocarbon recovery.

The olefin sulfonates described herein can be produced by the sulfonation of propylene oligomers, which in turn can be produced by the oligomerization of propylene monomers. Discussion of olefin sulfonates can be found in US App. No. 20090111717, U.S. Pat. Nos. 8,293,688, 4,597,879, 4,979, 564, 8,513,168, 9,284,481, 10,184,076, US App. No. 20080171672, US App. No. 20140224490, US App. No. 20100282467, U.S. Pat. Nos. 8,403,044, 8,889,600, US App. No. 20160304767, US App. No. 20120097389, U.S. Pat. No. 7,770,641, US App. No. 20180230788, which are hereby incorporated by reference.

An olefin feedstock comprising propylene can come from many different sources and have a wide range of compositional attributes. The feedstock for use in preparing the propylene oligomers will typically contain propylene in an amount of at least about 50 wt %, 60 wt %, 70 wt %, 80 wt %, 90 wt %, or 95 wt % based on the total weight of the feedstock.

In some cases, the feedstock can contain relatively low amounts, if any (i.e., substantially free), of olefin(s) other than propylene. For example, the feedstock can contain less than about 10 wt %, such as 9 wt %, 8 wt %, 7 wt %, 6 wt %, 5 wt %, 4 wt %, 3 wt %, 2 wt %, or 1 wt % of butene. The feedstock can also contain relatively low amounts, typically less than about 10 wt %, such as 9 wt %, 8 wt %, 7 wt %, 6 wt %, 5 wt %, 4 wt %, 3 wt %, 2 wt %, or 1 wt % of non-reactive components such as alkanes, e.g., ethane, propane, butane, isobutane and the like.

The oligomerization process involves polymerization of propylene in the presence of a liquid phosphoric acid or ionic liquid catalyst to obtain propylene oligomer products suitable for making olefin sulfonates described herein. A more detailed description of phosphoric acid catalysts can be found in U.S. Pat. Nos. 2,592,428, 2,814,655, 3,887,634, and 8,183,192, which are hereby incorporated by reference. A more detailed discussion of ionic liquid catalysts can be found in U.S. Pat. No. 9,938,473, which is hereby incorporated by reference.

Suitable propylene oligomer products include propylene pentamer and propylene tetramer. A "propylene tetramer" or $PP_4$ is an olefin oligomer product resulting from the oligomerization of nominally 4 propylene monomers. A "propylene pentamer" or $PP_5$ is an olefin oligomer product resulting from the oligomerization of nominally 5 propylene monomers. An unrefined product of the oligomerization process typically includes a mixture of branched olefins with a carbon distribution ranging from about $C_9$ to about $C_{50}$. The unrefined product can be distilled to further isolate or purify the olefin oligomer product to the preferred carbon range. According to some embodiments, the olefin oligomer product can comprise at least about 50 wt %, such as 60 wt %, 70 wt %, 75 wt %, 80 wt %, 85 wt %, 90 wt %, or 95 wt % $C_{12}$ to $C_{40}$ olefin oligomers (e.g., $C_{16}$ to $C_{30}$ olefin oligomers). According to some embodiments, the olefin oligomer product can comprise at least about 50 wt %, such as 60 wt %, 70 wt %, 75 wt %, 80 wt %, 85 wt %, 90 wt %, or 95 wt % $C_{31}$ to $C_{50}$ olefin oligomers (e.g., $C_{31}$ to $C_{40}$ olefin oligomers).

The olefin oligomer can be dimerized to form dimers that are also suitable for sulfonation and subsequent use as surfactants. Examples of dimers include a dimer of propylene tetramer or $(PP_4)_2$ and a dimer of propylene pentamer or $(PP_5)_2$. The dimers can be sulfonated and subsequently used as surfactants.

As an illustrative example, the propylene oligomer product can be obtained by contacting a feedstock comprising a major amount of propylene with a liquid phosphoric acid catalyst in a reaction zone under oligomerization conditions. In general, the feedstock and liquid phosphoric acid catalyst are contacted in the reaction zone at conditions sufficient to maintain a normally gaseous feedstock in a liquid state. Typically, the temperature of the reaction zone can be maintained between about 75° C. to about 175° C., such as 85° C. to 150° C., 100° C. to 150° C., or 110° C. to 125° C. The pressure can be maintained between about 200 psig to about 1600 psig, such as 400 psig to 1000 psig, 500 psig to 850 psig, or 550 psig to 800 psig.

As mentioned above, the normally gaseous hydrocarbon mixture comprising propylene can be introduced in liquid phase and under an elevated pressure into a body of liquid phosphoric acid and vigorously mixed with the acid at elevated temperatures. Propylene may be contacted with the acid at a rate of at least 0.15 volumes of liquid propylene per volume of acid per hour, and conversion of propylene to liquid polymer product is substantially in excess of 50% in a single pass operation. Generally, the feedstock and liquid phosphoric acid catalyst are contacted for a time period ranging from about 5 minutes to about 45 minutes. The conversion rate of the propylene (weight percent oligomerized product/total weight of starting olefin) is at least about 50 wt %, such as 55 wt %, 60 wt %, 65 wt %, 70 wt %, 75 wt %, 80 wt %, 85 wt %, 90 wt %, or 95 wt %.

The phosphoric acid catalyst strength can vary, but should be sufficient to produce propylene oligomer with an initial boiling point of at least about 160° C. In some embodiments, the acid strength is above about 105%, such as 106%, 107%, 108%, 109%, 110%, or 111%. In some embodiments, the acid strength is below about 125%, such as 124%, 123%, 122%, 121%, 120%, 119%, 118%, 117%, 116%, 115%, 114%, or 113%. The isolated propylene oligomer can have an initial boiling point of about 160° C. (5% boiling point is about 180° C.) and a final boiling point of about 225° C. as measured by ASTM D86.

The strength of the phosphoric acid catalyst can be calculated by, for example, measuring the polyphosphoric acid peaks using NMR (nuclear magnetic resonance spectroscopy), and can be expressed as a percentage of $P_2O_5$ greater than that required for the hydrolysis reaction to make orthophosphoric acid ($H_3PO_4$). Orthophosphoric acid will have a strength of 100%, pyrophosphoric acid ($H_4P_2O_7$) will have a strength of 110%, and polyphosphoric acid $H_4P_2O_7$ ($HPO_3$)n, will have a strength of 114% when n is 1 and a strength of 116% when n is 2.

As an illustrative example, ionic liquid catalysts are typically composed of at least two components that form a complex (e.g., a first component and a second component). The first component may comprise a Lewis Acid while the second component may comprise organic salt or mixture of salts. A co-catalyst (e.g., HCl, organic chlorides, hydrogen halides, etc.) may also be present.

The oligomerization via ionic liquid catalysts may be performed under a wide range of conditions. For example, the oligomerization reaction can be conducted under a pressure of about 100-1000 psig (689-6895 kPa). In certain embodiments, the oligomerization reaction is conducted under a pressure of about 350-700 psig (2413 kPa-4826 kPa). In certain embodiments, the oligomerization reaction is conducted under a pressure of 400-500 psig (2758 kPa-3447 kPa). In certain embodiments, the oligomerization reaction is conducted under a pressure of about 400 (2758 kPa), 450 (3103 kPa), 470 (3241 kPa) or 500 psig (3447 kPa). The oligomerization reaction temperature can range from about 10° C. to about 149° C., such as from about 24° C. to about 135° C., from about 38° C. to about 121° C. In one embodiment, the oligomerization temperature is about 38° C., 49° C., 50° C., 52° C., 54° C., or 66° C.

As alluded to above, the olefin oligomer may be dimerized prior to the sulfonation step. The dimerization process generally involves treating the olefin oligomers with one or more suitable catalysts.

In one embodiment, the dimerization catalyst is an acid catalyst including Brønsted acids such as hydrogen fluoride, phosphoric acid, and the like. Other acid catalysts include Lewis acids such as boron trifluoride, aluminum chloride, organoflourophosphonium salts, bismuth, and the like.

In some cases, the dimerization catalyst may be an inorganic or organometallic coordination complex based on nickel, group IV metals such as titanium, zirconium, and hafnium, aluminum, iridium, tantalum, tungsten, and the like.

In some cases, the dimerization catalyst may be an acidic clay such as montmorillonites, bentonites, or F-20X commercially available from BASF Corporation (Florham Park, NJ) and F-24X commercially available BASF (Florham Park, NJ). The dimerization catalyst may also be a solid supported acid catalyst such as Amberlyst™ A36 commercially available from Dow (Midland, MI), zeolite materials, alumina, and the like.

During the dimerization process, the olefin oligomer is typically charged with a catalyst whose loading can range from about 0.5 wt % to about 50 wt %, such as 1 wt % to 10 wt %, 11 wt % to 20 wt %, 21 wt % to 30 wt %, 31 wt % to 40 wt %, or 41 wt % to 50 wt %.

The olefin oligomer and catalyst are generally agitated by stirring, placed in an inert atmosphere like under nitrogen or argon and so forth, and then heated to the desired temperature. The temperature of the dimerization process can range from about 50° C. to about 300° C., such as 50° C. to 250° C., or 100° C. to 200° C. The dimerization process is typically heated from about 0.1 h to 300 h, such as 10 h to 250 h, 50 h to 200 h, or 100 h to 150 h. The dimerized olefin oligomer can be further isolated or purified by removing the unreacted oligomers by distillation.

In some cases, the dimerization can be conducted in a continuous unit, where the olefin is fed through a fixed bed solid acid catalyst. The temperature of the continuous dimerization process can range from about 50° C. to 300° C., such as 50° C. to 250° C., or 100° C. to 200° C. The dimerization process is typically heated from about 0.1 h to 300 h, such as 10 h to 250 h, 50 h to 200 h, or 100 h to 150 h. The dimerized olefin oligomer can be further isolated or purified by removing the unreacted oligomers by distillation.

A sulfonation process can involve treating olefin oligomers with $SO_3$ gas in the presence of air. Air/$SO_3$ sulfonation process is a direct process in which $SO_3$ gas is diluted with air and reacted directly with the olefin. The source of the $SO_3$ gas may be from various sources. These sources include sulfuric acid plant converter gas, $SO_3$ from boiling concentrated oleum, liquid $SO_3$, converting $SO_2$ into $SO_3$ via catalytic oxidation, and sulfur burning in equipment specifically designed to produce $SO_3$ gas for sulfonation.

For an industrial process, this process usually involves treating an organic feedstock with $SO_3$ that has been diluted with air in a reactor (typically film reactor). The air is typically dried and supplied by an air supply system. For isomerized and internal olefin sulfonates, the sulfonation reaction typically occurs at the alkene, and can take place at any place along the chain since its double bond is randomly distributed. In generally, process variables such as mole ratio of $SO_3$ to feedstock, temperature, and concentration can impact quality of product. For example, because sulfonation is a rapid exothermic reaction, optimizing the ratio of $SO_3$ to feedstock can help control the rate of reaction and minimize undesirable by-products.

With respect to process variables, any compatible range of parameters may be used. In some embodiments, the mole ratio of $SO_3$ to air can range from about 0.8 to about 1.6, such as 0.85 to 1.5, 0.9 to 1.2, or 0.95 to 1.15. The $SO_3$ inlet gas concentration can range from about 0.1% to about 10%, such as 0.5% to 9%, 1% to 8%, 2% to 7%, 3% to 6%, or 4% to 5%. The reaction temperature can range from about 0° C. to about 80° C., such as 10° C. to 60° C., 20° C. to 40° C., or 25° C. to 35° C.

After the initial treatment of the olefin oligomer with $SO_3$, the resulting mixture is neutralized with a base. Neutralization of the olefin sulfonic acid may be carried out in a continuous or batch process by any method known to one skilled in the art to produce the olefin sulfonate. Typically, an olefin sulfonic acid is neutralized by a base with a mono-covalent cation (e.g., an alkali metal such as sodium, lithium, potassium, ammonium or substituted ammonium ion). Aqueous 50% sodium hydroxide is a common neutralizing agent. Next the mixture can be hydrolyzed at ambient or elevated temperatures to convert any remaining sulfones to alkene sulfonates and hydroxy sulfonates. The neutralization can occur at temperatures from about 20° C. to about 100° C., such as 30° C. to 90° C., 40° C. to 80° C., or 50° C. to 70° C. This results in an aqueous solution of olefin sulfonates. Optionally, the neutralized olefin sulfonate may be further hydrolyzed with additional base or caustic.

The propylene oligomer products of the present invention can have an average carbon number between 9 to 50, 10 to 35, or 12 to 30. The propylene oligomer products of the present invention generally have higher branching compared to other internal olefin sulfonates or isomerized olefin sulfonates, which are based on ethylene oligomers. The propylene oligomerization process results in a more naturally branched material, which obviates the need for a separate isomerization process which is commonly needed for oligomerized ethylene olefins. A more detailed description of isomerized olefin sulfonates can be found in U.S. Pat. No. 8,993,798, which is hereby incorporated by reference.

$^1$H NMR can be employed to characterize the degree of branching or average number of branches per chain. Total branching is the sum of aliphatic branching and olefinic branching. Aliphatic branching is the degree of branching at the aliphatic carbons while olefinic branching is the degree of branching at the olefinic carbons. While most conventional internal/isomerized olefin sulfonates have an average total branching below 3, the present invention provides internal olefin sulfonates with higher branching levels. The higher branched internal olefin sulfonates may have physical properties that are more desirable in surfactant applications. A more detailed description of NMR branching analysis can be found in US Pat. No. 20080171672, which is hereby incorporated by reference.

Surfactant Packages

The present disclosure also provides surfactant packages that comprise an olefin sulfonate described herein. Example surfactant packages can comprise a primary surfactant and optionally one or more secondary surfactants, where at least one of the surfactants (e.g., the primary surfactant, a secondary surfactant, or any combination thereof) comprises an olefin sulfonate surfactant described herein.

In some embodiments, the primary surfactant can comprise an olefin sulfonate surfactant as described herein, and the optional one or more secondary surfactants can be selected from an anionic surfactant, a cationic surfactant, a zwitterionic surfactant, an amphoteric surfactant, or a non-ionic surfactant. In other embodiments, the primary surfactant can comprise an anionic surfactant, a cationic surfactant, a zwitterionic surfactant, an amphoteric surfactant, or a non-ionic surfactant, and the secondary surfactant comprises an olefin sulfonate surfactant as described herein. In some embodiments, the surfactant package comprises a single-phase liquid surfactant package.

In some embodiments, the primary surfactant can comprise at least 10% by weight (e.g., at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, or at least 85% by weight) of the surfactant package, based on the total weight of the surfactant package. In some embodiments, the primary surfactant can comprise 90% by weight or less (e.g., 85% by weight or less, 80% by weight or less, 75% by weight or less, 70% by weight or less, 65% by weight or less, 60% by weight or less, 55% by weight or less, 50% by weight or less, 45% by weight or less, 40% by weight or less, 35% by weight or less, 30% by weight or less, 25% by weight or less, 20% by weight or less, or 15% by weight or less) of the surfactant package, based on the total weight of the surfactant package.

The primary surfactant can be present in the surfactant package in an amount ranging from any of the minimum values described above to any of the maximum values described above. For example, in some embodiments, the primary surfactant can comprise from 10% to 90% by weight (e.g., from 10% to 50% by weight) of the surfactant package, based on the total weight of the single-phase liquid surfactant package.

In some embodiments, the one or more secondary surfactants can comprise at least 10% by weight (e.g., at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, or at least 85% by weight) of the surfactant package, based on the total weight of the surfactant package. In some embodiments, the one or more secondary surfactants can comprise 90% by weight or less (e.g., 85% by weight or less, 80% by weight or less, 75% by weight or less, 70% by weight or less, 65% by weight or less, 60% by weight or less, 55% by weight or less, 50% by weight or less, 45% by weight or less, 40% by weight or less, 35% by weight or less, 30% by weight or less, 25% by weight or less, 20% by weight or less, or 15% by weight or less) of the surfactant package, based on the total weight of the single-phase liquid surfactant package.

The one or more secondary surfactants can be present in the surfactant package in an amount ranging from any of the minimum values described above to any of the maximum values described above. For example, in some embodiments, the one or more secondary surfactants can comprise from 10% to 90% by weight (e.g., from 10% to 50% by weight) of the surfactant package, based on the total weight of the surfactant package.

In some embodiments, the surfactant package can comprise an olefin sulfonate as described herein. In other embodiments, the surfactant package can consist essentially of an olefin sulfonate as described herein (i.e., the olefin sulfonate is the only surfactant present in the surfactant package). In some embodiments, the surfactant package can consist of an olefin sulfonate as described herein. In some embodiments, the surfactant package further includes water. In some of these embodiments, the surfactant package does not comprise a hydrocarbon.

In some embodiments, the surfactant package can comprise an olefin sulfonate as described herein and a second anionic surfactant. In some embodiments, the surfactant package can consist essentially of an olefin sulfonate as described herein and a second anionic surfactant (i.e., the olefin sulfonate and second anionic surfactant are the only surfactants present in the surfactant package). In some embodiments, the surfactant package consists of an olefin sulfonate as described herein and a second anionic surfactant. In some embodiments, the olefin sulfonate as described herein is the primary surfactant. In some embodiments, the olefin sulfonate as described herein is a secondary surfactant. In some embodiments, the surfactant package further includes water. In some embodiments, the surfactant package does not comprise a hydrocarbon.

In some embodiments, the surfactant package can comprise an olefin sulfonate as described herein and a non-ionic surfactant. In some embodiments, the surfactant package can consist essentially of an olefin sulfonate as described herein and a non-ionic surfactant (i.e., the olefin sulfonate and the non-ionic surfactant are the only surfactants present in the surfactant package). In some embodiments, the surfactant package consists of an olefin sulfonate as described herein and a non-ionic surfactant. In some embodiments, the olefin sulfonate as described herein is the primary surfactant. In some embodiments, the olefin sulfonate as described herein is a secondary surfactant. In some embodiments, the surfactant package further includes water. In some embodiments, the surfactant package does not comprise a hydrocarbon.

In some embodiments, the surfactant package can comprise an olefin sulfonate as described herein and a cationic surfactant. In some embodiments, the surfactant package can consist essentially of an olefin sulfonate as described herein and a cationic surfactant (i.e., the olefin sulfonate and the cationic surfactant are the only surfactants present in the surfactant package). In some embodiments, the surfactant package consists of an olefin sulfonate as described herein and a cationic surfactant. In some embodiments, the olefin sulfonate as described herein is the primary surfactant. In some embodiments, the olefin sulfonate as described herein is a secondary surfactant. In some embodiments, the surfactant package further includes water. In some embodiments, the surfactant package does not comprise a hydrocarbon.

In some embodiments, the surfactant package can comprise an olefin sulfonate as described herein and a zwitterionic surfactant. In some embodiments, the surfactant package can consist essentially of an olefin sulfonate as described herein and a zwitterionic surfactant (i.e., the olefin sulfonate and the zwitterionic surfactant are the only surfactants present in the surfactant package). In some embodiments, the surfactant package consists of an olefin sulfonate as described herein and a zwitterionic surfactant. In some embodiments, the olefin sulfonate as described herein is the primary surfactant. In some embodiments, the olefin sulfonate as described herein is a secondary surfactant. In some embodiments, the surfactant package further includes water. In some embodiments, the surfactant package does not comprise a hydrocarbon.

In some embodiments, the surfactant package can comprise an olefin sulfonate as described herein and an amphoteric surfactant. In some embodiments, the surfactant package can consist essentially of an olefin sulfonate as described herein and an amphoteric surfactant (i.e., the olefin sulfonate and the amphoteric surfactant are the only surfactants present in the surfactant package). In some embodiments, the surfactant package consists of an olefin sulfonate as described herein and an amphoteric surfactant. In some embodiments, the olefin sulfonate as described herein is the primary surfactant. In some embodiments, the olefin sulfonate as described herein is a secondary surfactant. In some embodiments, the surfactant package further includes water. In some embodiments, the surfactant package does not comprise a hydrocarbon.

Suitable anionic surfactants for use as a primary surfactant and/or a secondary surfactant include a hydrophobic tail that comprises from 6 to 60 carbon atoms. In some embodiments, the anionic surfactant can include a hydrophobic tail that comprises at least 6 carbon atoms (e.g., at least 7 carbon atoms, at least 8 carbon atoms, at least 9 carbon atoms, at least 10 carbon atoms, at least 11 carbon atoms, at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, at least 20 carbon atoms, at least 21 carbon atoms, at least 22 carbon atoms, at least 23 carbon atoms, at least 24 carbon atoms, at least 25 carbon atoms, at least 26 carbon atoms, at least 27 carbon atoms, at least 28 carbon atoms, at least 29 carbon atoms, at least 30 carbon atoms, at least 31 carbon atoms, at least 32 carbon atoms, at least 33 carbon atoms, at least 34 carbon atoms, at least 35 carbon atoms, at least 36 carbon atoms, at least 37 carbon atoms, at least 38 carbon atoms, at least 39 carbon atoms, at least 40 carbon atoms, at least 41 carbon atoms, at least 42 carbon atoms, at least 43 carbon atoms, at least 44 carbon atoms, at least 45 carbon atoms, at least 46 carbon atoms, at least 47 carbon atoms, at least 48 carbon atoms, at least 49 carbon atoms, at least 50 carbon atoms, at least 51 carbon atoms, at least 52 carbon atoms, at least 53 carbon atoms, at least 54 carbon atoms, at least 55 carbon atoms, at least 56 carbon atoms, at least 57 carbon atoms, at least 58 carbon atoms, or at least 59 carbon atoms). In some embodiments, the anionic surfactant can include a hydrophobic tail that comprises 60 carbon atoms or less (e.g., 59 carbon atoms or less, 58 carbon atoms or less, 57 carbon atoms or less, 56 carbon atoms or less, 55 carbon atoms or less, 54 carbon atoms or less, 53 carbon atoms or less, 52 carbon atoms or less, 51 carbon atoms or less, 50 carbon atoms or less, 49 carbon atoms or less, 48 carbon atoms or less, 47 carbon atoms or less, 46 carbon atoms or less, 45 carbon atoms or less, 44 carbon atoms or less, 43 carbon atoms or less, 42 carbon atoms or less, 41 carbon atoms or less, 40 carbon atoms or less, 39 carbon atoms or less, 38 carbon atoms or less, 37 carbon atoms or less, 36 carbon atoms or less, 35 carbon atoms or less, 34 carbon atoms or less, 33 carbon atoms or less, 32 carbon atoms or less, 31 carbon atoms or less, 30 carbon atoms or less, 29 carbon atoms or less, 28 carbon atoms or less, 27 carbon atoms or less, 26 carbon atoms or less, 25 carbon atoms or less, 24 carbon atoms or less, 23 carbon atoms or less, 22 carbon atoms or less, 21 carbon atoms or less, 20 carbon atoms or less, 19 carbon atoms or less, 18 carbon atoms or less, 17 carbon atoms or less, 16 carbon atoms or less, 15 carbon atoms or less, 14 carbon atoms or less, 13 carbon atoms or less, 12 carbon atoms or less, 11 carbon atoms or less, 10 carbon atoms or less, 9 carbon atoms or less, 8 carbon atoms or less, or 7 carbon atoms or less).

The anionic surfactant can include a hydrophobic tail that comprises a number of carbon atoms ranging from any of the minimum values described above to any of the maximum values described above. For example, in some embodiments, the anionic surfactant can comprise a hydrophobic tail comprising from 6 to 15, from 16 to 30, from 31 to 45, from 46 to 60, from 6 to 25, from 26 to 60, from 6 to 30, from 31 to 60, from 6 to 32, from 33 to 60, from 6 to 12, from 13 to 22, from 23 to 32, from 33 to 42, from 43 to 52, from 53 to 60, from 6 to 10, from 10 to 15, from 16 to 25, from 26 to 35, or from 36 to 45 carbon atoms. The hydrophobic (lipophilic) carbon tail may be a straight chain, branched chain, and/or may comprise cyclic structures. The hydrophobic carbon tail may comprise single bonds, double bonds, triple bonds, or any combination thereof. In some embodiments, the anionic surfactant can include a branched hydrophobic tail derived from Guerbet alcohols. The hydrophilic portion of the anionic surfactant can comprise, for example, one or more sulfate moieties (e.g., one, two, or three sulfate moieties), one or more sulfonate moieties (e.g., one, two, or three sulfonate moieties), one or more sulfosuccinate moieties (e.g., one, two, or three sulfosuccinate moieties), one or more carboxylate moieties (e.g., one, two, or three carboxylate moieties), or any combination thereof.

In some embodiments, the anionic surfactant can comprise, for example a sulfonate, a disulfonate, a polysulfonate, a sulfate, a disulfate, a polysulfate, a sulfosuccinate, a disulfosuccinate, a polysulfosuccinate, a carboxylate, a dicarboxylate, a polycarboxylate, or any combination thereof. In some examples, the anionic surfactant can comprise an internal olefin sulfonate (IOS) other than the olefin sulfonates described herein, an isomerized olefin sulfonate, an alfa olefin sulfonate (AOS), an alkyl aryl sulfonate (AAS), a xylene sulfonate, an alkane sulfonate, a petroleum sulfonate, an alkyl diphenyl oxide (di)sulfonate, an alcohol sulfate, an alkoxy sulfate, an alkoxy sulfonate, an alkoxy carboxylate, an alcohol phosphate, or an alkoxy phosphate. In some embodiments, the anionic surfactant can comprise an alkoxy carboxylate surfactant, an alkoxy sulfate surfactant, an alkoxy sulfonate surfactant, an alkyl sulfonate surfactant, an aryl sulfonate surfactant, or an olefin sulfonate surfactant.

An "alkoxy carboxylate surfactant" or "alkoxy carboxylate" refers to a compound having an alkyl or aryl attached to one or more alkoxylene groups (typically —CH$_2$—CH(ethyl)-O—, —CH$_2$—CH(methyl)-O—, or —CH$_2$—CH$_2$—O—) which, in turn is attached to —COO$^-$ or acid or salt thereof including metal cations such as sodium. In embodiments, the alkoxy carboxylate surfactant can be defined by the formulae below:

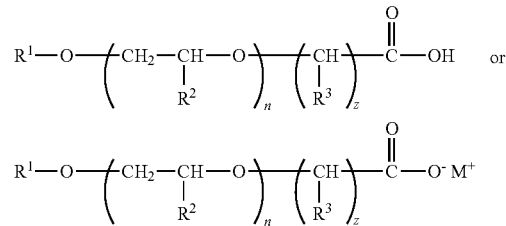

wherein R$^1$ is substituted or unsubstituted C6-C36 alkyl or substituted or unsubstituted aryl; R$^2$ is, independently for each occurrence within the compound, hydrogen or unsubstituted C1-C6 alkyl; R$^3$ is independently hydrogen or unsubstituted C1-C6 alkyl, n is an integer from 0 to 175, z is an integer from 1 to 6 and M$^+$ is a monovalent, divalent or trivalent cation. In some of these embodiments, R$^1$ can be an unsubstituted linear or branched C6-C36 alkyl.

In certain embodiments, the alkoxy carboxylate can be a C6-C32:PO(0-65):EO(0-100)-carboxylate (i.e., a C6-C32 hydrophobic tail, such as a branched or unbranched C6-C32 alkyl group, attached to from 0 to 65 propyleneoxy groups (—CH$_2$—CH(methyl)-O— linkers), attached in turn to from 0 to 100 ethyleneoxy groups (—CH$_2$—CH$_2$—O— linkers), attached in turn to —COO$^-$ or an acid or salt thereof including metal cations such as sodium). In certain embodiments, the alkoxy carboxylate can be a branched or unbranched C6-C30:PO(30-40):EO(25-35)-carboxylate. In certain embodiments, the alkoxy carboxylate can be a branched or unbranched C6-C12:PO(30-40):EO(25-35)-carboxylate. In certain embodiments, the alkoxy carboxylate can be a branched or unbranched C6-C30:EO(8-30)-carboxylate.

An "alkoxy sulfate surfactant" or "alkoxy sulfate" refers to a surfactant having an alkyl or aryl attached to one or more alkoxylene groups (typically —$CH_2$—CH(ethyl)-O—, —$CH_2$—CH(methyl)-O—, or —$CH_2$—$CH_2$—O—) which, in turn is attached to —$SO_3^-$ or acid or salt thereof including metal cations such as sodium. In some embodiment, the alkoxy sulfate surfactant has the formula R—$(BO)_e$—$(PO)_f$-$(EO)_g$—$SO_3^-$ or acid or salt (including metal cations such as sodium) thereof, wherein R is C6-C32 alkyl, BO is —$CH_2$—CH(ethyl)-O—, PO is —$CH_2$—CH(methyl)-O—, and EO is —$CH_2$—$CH_2$—O—. The symbols e, f and g are integers from 0 to 50 wherein at least one is not zero.

In embodiments, the alkoxy sulfate surfactant can be an aryl alkoxy sulfate surfactant. The aryl alkoxy surfactant can be an alkoxy surfactant having an aryl attached to one or more alkoxylene groups (typically —$CH_2$—CH(ethyl)-O—, —$CH_2$—CH(methyl)-O—, or —$CH_2$—$CH_2$—O—) which, in turn is attached to —$SO_3^-$ or acid or salt thereof including metal cations such as sodium.

An "alkyl sulfonate surfactant" or "alkyl sulfonate" refers to a compound that includes an alkyl group (e.g., a branched or unbranched C6-C32 alkyl group) attached to —$SO_3^-$ or acid or salt thereof including metal cations such as sodium.

An "aryl sulfate surfactant" or "aryl sulfate" refers to a compound having an aryl group attached to —O—$SO_3^-$ or acid or salt thereof including metal cations such as sodium. An "aryl sulfonate surfactant" or "aryl sulfonate" refers to a compound having an aryl group attached to —$SO_3^-$ or acid or salt thereof including metal cations such as sodium. In some cases, the aryl group can be substituted, for example, with an alkyl group (an alkyl aryl sulfonate).

An "internal olefin sulfonate," "isomerized olefin sulfonate," or "IOS" in the context of co-surfactants present in addition to the olefin sulfonates described herein refers to an unsaturated hydrocarbon compound comprising at least one carbon-carbon double bond and at least one $SO_3^-$ group, or a salt thereof. As used herein, a "C20-C28 internal olefin sulfonate," "a C20-C28 isomerized olefin sulfonate," or "C20-C28 IOS" refers to an IOS, or a mixture of IOSs with an average carbon number of 20 to 28, or of 23 to 25. The C20-C28 IOS may comprise at least 80% of IOS with carbon numbers of 20 to 28, at least 90% of IOS with carbon numbers of 20 to 28, or at least 99% of IOS with carbon numbers of 20 to 28. As used herein, a "$C_{15}$-$C_{18}$ internal olefin sulfonate," "C15-C18 isomerized olefin sulfonate," or "C15-C18 IOS" refers to an IOS or a mixture of IOSs with an average carbon number of 15 to 18, or of 16 to 17. The C15-C18 IOS may comprise at least 80% of IOS with carbon numbers of 15 to 18, at least 90% of IOS with carbon numbers of 15 to 18, or at least 99% of IOS with carbon numbers of 15 to 18. The internal olefin sulfonates or isomerized olefin sulfonates may be alpha olefin sulfonates, such as an isomerized alpha olefin sulfonate. The internal olefin sulfonates or isomerized olefin sulfonates may also comprise branching. In certain embodiments, C15-18 IOS may be added to surfactant packages described herein when used for LPS injection fluids intended for use in high temperature unconventional subterranean formations, such as formations above 130° F. (approximately 55° C.). The IOS may be at least 20% branching, 30% branching, 40% branching, 50% branching, 60% branching, or 65% branching. In some embodiments, the branching is between 20-98%, 30-90%, 40-80%, or around 65%. Examples of internal olefin sulfonates and the methods to make them are found in U.S. Pat. No. 5,488,148, U.S. Patent Application Publication 2009/0112014, and SPE 129766, all incorporated herein by reference.

In embodiments, the anionic surfactant can be a disulfonate, alkyldiphenyloxide disulfonate, mono alkyldiphenyloxide disulfonate, di alkyldiphenyloxide disulfonate, or a di alkyldiphenyloxide monosulfonate, where the alkyl group can be a C6-C36 linear or branched alkyl group. In embodiments, the anionic surfactant can be an alkylbenzene sulfonate or a dibenzene disulfonate. In embodiments, the anionic surfactant can be benzenesulfonic acid, decyl(sulfophenoxy)-disodium salt; linear or branched C6-C36 alkyl:PO(0-65):EO(0-100) sulfate; or linear or branched C6-C36 alkyl:PO(0-65):EO(0-100) carboxylate. In embodiments, the anionic surfactant is an isomerized olefin sulfonate (C6-C30), internal olefin sulfonate (C6-C30) or internal olefin disulfonate (C6-C30). In some embodiments, the anionic surfactant is a Guerbet-PO(0-65)-EO(0-100) sulfate (Guerbet portion can be C6-C36). In some embodiments, the anionic surfactant is a Guerbet-PO(0-65)-EO(0-100) carboxylate (Guerbet portion can be C6-C36). In some embodiments, the anionic surfactant is alkyl PO(0-65) and EO(0-100) sulfonate: where the alkyl group is linear or branched C6-C36. In some embodiments, the anionic surfactant is a sulfosuccinate, such as a dialkylsulfosuccinate. In some embodiments, the anionic surfactant is an alkyl aryl sulfonate (AAS) (e.g. an alkyl benzene sulfonate (ABS)), a C10-C30 internal olefin sulfate (IOS), a petroleum sulfonate, or an alkyl diphenyl oxide (di)sulfonate.

In some examples, the anionic surfactant can comprise a surfactant defined by the formula below:

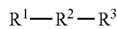

wherein $R^1$ comprises a branched or unbranched, saturated or unsaturated, cyclic or non-cyclic, hydrophobic carbon chain having 6-32 carbon atoms and an oxygen atom linking $R^1$ and $R^2$; $R^2$ comprises an alkoxylated chain comprising at least one oxide group selected from the group consisting of ethylene oxide, propylene oxide, butylene oxide, or any combination thereof; and $R^3$ comprises a branched or unbranched hydrocarbon chain comprising 2-12 carbon atoms and from 2 to 5 carboxylate groups.

In some examples, the anionic surfactant can comprise a surfactant defined by the formula below:

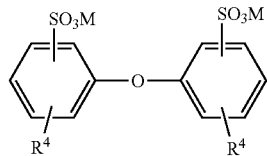

wherein $R^4$ is, independently for each occurrence, a branched or unbranched, saturated or unsaturated, cyclic or non-cyclic, hydrophobic carbon chain having 6-32 carbon atoms; and M represents a counterion (e.g., $Na^+$, $K^+$). In some embodiments, $R^4$ is a branched or unbranched, saturated or unsaturated, cyclic or non-cyclic, hydrophobic carbon chain having 6-16 carbon atoms.

In some embodiments, non-ionic surfactants may be used as the primary surfactant and/or secondary surfactant. Suitable non-ionic surfactants include compounds that can be added to increase wettability. In some embodiments, the hydrophilic-lipophilic balance (HLB) of the non-ionic surfactant is greater than 10 (e.g., greater than 9, greater than 8, or greater than 7). In some embodiments, the HLB of the non-ionic surfactant is from 7 to 10.

The non-ionic surfactant can comprise a hydrophobic tail comprising from 6 to 60 carbon atoms. In some embodiments, the non-ionic surfactant can include a hydrophobic tail that comprises at least 6 carbon atoms (e.g., at least 7 carbon atoms, at least 8 carbon atoms, at least 9 carbon atoms, at least 10 carbon atoms, at least 11 carbon atoms, at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, at least 20 carbon atoms, at least 21 carbon atoms, at least 22 carbon atoms, at least 23 carbon atoms, at least 24 carbon atoms, at least 25 carbon atoms, at least 26 carbon atoms, at least 27 carbon atoms, at least 28 carbon atoms, at least 29 carbon atoms, at least 30 carbon atoms, at least 31 carbon atoms, at least 32 carbon atoms, at least 33 carbon atoms, at least 34 carbon atoms, at least 35 carbon atoms, at least 36 carbon atoms, at least 37 carbon atoms, at least 38 carbon atoms, at least 39 carbon atoms, at least 40 carbon atoms, at least 41 carbon atoms, at least 42 carbon atoms, at least 43 carbon atoms, at least 44 carbon atoms, at least 45 carbon atoms, at least 46 carbon atoms, at least 47 carbon atoms, at least 48 carbon atoms, at least 49 carbon atoms, at least 50 carbon atoms, at least 51 carbon atoms, at least 52 carbon atoms, at least 53 carbon atoms, at least 54 carbon atoms, at least 55 carbon atoms, at least 56 carbon atoms, at least 57 carbon atoms, at least 58 carbon atoms, or at least 59 carbon atoms). In some embodiments, the non-ionic surfactant can include a hydrophobic tail that comprises 60 carbon atoms or less (e.g., 59 carbon atoms or less, 58 carbon atoms or less, 57 carbon atoms or less, 56 carbon atoms or less, 55 carbon atoms or less, 54 carbon atoms or less, 53 carbon atoms or less, 52 carbon atoms or less, 51 carbon atoms or less, 50 carbon atoms or less, 49 carbon atoms or less, 48 carbon atoms or less, 47 carbon atoms or less, 46 carbon atoms or less, 45 carbon atoms or less, 44 carbon atoms or less, 43 carbon atoms or less, 42 carbon atoms or less, 41 carbon atoms or less, 40 carbon atoms or less, 39 carbon atoms or less, 38 carbon atoms or less, 37 carbon atoms or less, 36 carbon atoms or less, 35 carbon atoms or less, 34 carbon atoms or less, 33 carbon atoms or less, 32 carbon atoms or less, 31 carbon atoms or less, 30 carbon atoms or less, 29 carbon atoms or less, 28 carbon atoms or less, 27 carbon atoms or less, 26 carbon atoms or less, 25 carbon atoms or less, 24 carbon atoms or less, 23 carbon atoms or less, 22 carbon atoms or less, 21 carbon atoms or less, 20 carbon atoms or less, 19 carbon atoms or less, 18 carbon atoms or less, 17 carbon atoms or less, 16 carbon atoms or less, 15 carbon atoms or less, 14 carbon atoms or less, 13 carbon atoms or less, 12 carbon atoms or less, 11 carbon atoms or less, 10 carbon atoms or less, 9 carbon atoms or less, 8 carbon atoms or less, or 7 carbon atoms or less).

The non-ionic surfactant can include a hydrophobic tail that comprises a number of carbon atoms ranging from any of the minimum values described above to any of the maximum values described above. For example, the non-ionic surfactant can comprise a hydrophobic tail comprising from 6 to 15, from 16 to 30, from 31 to 45, from 46 to 60, from 6 to 25, from 26 to 60, from 6 to 30, from 31 to 60, from 6 to 32, from 33 to 60, from 6 to 12, from 13 to 22, from 23 to 32, from 33 to 42, from 43 to 52, from 53 to 60, from 6 to 10, from 10 to 15, from 16 to 25, from 26 to 35, or from 36 to 45 carbon atoms. In some cases, the hydrophobic tail may be a straight chain, branched chain, and/or may comprise cyclic structures. The hydrophobic carbon tail may comprise single bonds, double bonds, triple bonds, or any combination thereof. In some cases, the hydrophobic tail can comprise an alkyl group, with or without an aromatic ring (e.g., a phenyl ring) attached to it. In some embodiments, the hydrophobic tail can comprise a branched hydrophobic tail derived from Guerbet alcohols.

Example non-ionic surfactants include alkyl aryl alkoxy alcohols, alkyl alkoxy alcohols, or any combination thereof. In embodiments, the non-ionic surfactant may be a mix of surfactants with different length lipophilic tail chain lengths. For example, the non-ionic surfactant may be C9-C11:9EO, which indicates a mixture of non-ionic surfactants that have a lipophilic tail length of 9 carbon to 11 carbon, which is followed by a chain of 9 EOs. The hydrophilic moiety is an alkyleneoxy chain (e.g., an ethoxy (EO), butoxy (BO) and/or propoxy (PO) chain with two or more repeating units of EO, BO, and/or PO). In some embodiments, 1-100 repeating units of EO are present. In some embodiments, 0-65 repeating units of PO are present. In some embodiments, 0-25 repeating units of BO are present. For example, the non-ionic surfactant could comprise 10EO:5PO or 5EO. In embodiments, the non-ionic surfactant may be a mix of surfactants with different length lipophilic tail chain lengths. For example, the non-ionic surfactant may be C9-C11:PO9:EO2, which indicates a mixture of non-ionic surfactants that have a lipophilic tail length of 9 carbon to 11 carbon, which is followed by a chain of 9 POs and 2 EOs. In specific embodiments, the non-ionic surfactant is linear C9-C11:9EO. In some embodiments, the non-ionic surfactant is a Guerbet PO(0-65) and EO(0-100) (Guerbet can be C6-C36); or alkyl PO(0-65) and EO(0-100): where the alkyl group is linear or branched C1-C36. In some examples, the non-ionic surfactant can comprise a branched or unbranched C6-C32:PO(0-65):EO(0-100) (e.g., a branched or unbranched C6-C30:PO(30-40):EO(25-35), a branched or unbranched C6-C12:PO(30-40):EO(25-35), a branched or unbranched C6-30:EO(8-30), or any combination thereof),In some embodiments, the non-ionic surfactant is one or more alkyl polyglucosides.

Example cationic surfactants include surfactant analogous to those described above, except bearing primary, secondary, or tertiary amines, or quaternary ammonium cations, as a hydrophilic head group. "Zwitterionic" or "zwitterion" as used herein refers to a neutral molecule with a positive (or cationic) and a negative (or anionic) electrical charge at different locations within the same molecule. Example zwitterionic surfactants include betains and sultains.

Examples of suitable surfactants are disclosed, for example, in U.S. Pat. Nos. 3,811,504, 3,811,505, 3,811,507, 3,890,239, 4,463,806, 6,022,843, 6,225,267, 7,629,299, 7,770,641, 9,976,072, 8,211, 837, 9,422,469, 9,605,198, 10,233,382, and 9,617,464; WIPO Patent Application Nos. WO/2008/079855, WO/2012/027757 and WO/2011/094442; as well as U.S. Patent Application Nos. 2005/0199395, 2006/0185845, 2006/0189486, 2009/0270281, 2011/0046024, 2011/0100402, 2011/0190175, 2007/0191633, 2010/004843. 2011/0201531, 2011/0190174, 2011/0071057, 2011/0059873, 2011/0059872, 2011/0048721, 2010/0319920, 2010/0292110, 2019/0153299, and 2017/0198202, each of which is hereby incorporated by reference herein in its entirety for its description of example surfactants.

Optionally, the surfactant package can include one or more additional components. For example, the surfactant package can further comprise an acid, a polymer, a friction reducer, a gelling agent, a crosslinker, a scale inhibitor, a breaker, a pH adjusting agent, a non-emulsifier agent, an iron control agent, a corrosion inhibitor, a biocide, a clay stabilizing agent, a proppant, a wettability alteration chemical, a co-solvent (e.g., a C1-C5 alcohol, or an alkoxylated C1-C5 alcohol), or any combination thereof.

In some embodiments, the surfactant package can further include one or more co-solvents. Suitable co-solvents include alcohols, such as lower carbon chain alcohols such as isopropyl alcohol, ethanol, n-propyl alcohol, n-butyl alcohol, sec-butyl alcohol, n-amyl alcohol, sec-amyl alcohol, n-hexyl alcohol, sec-hexyl alcohol and the like; alcohol ethers, polyalkylene alcohol ethers, polyalkylene glycols, poly(oxyalkylene)glycols, poly(oxyalkylene)glycol ethers, ethoxylated phenol, or any other common organic co-solvent or any combination of any two or more co-solvents. In one embodiment, the co-solvent can comprise alkyl ethoxylate (C1-C6)-XEO X=1-30-linear or branched. In some embodiments, the co-solvent can comprise ethylene glycol butyl ether (EGBE), diethylene glycol monobutyl ether (DGBE), triethylene glycol monobutyl ether (TEGBE), ethylene glycol dibutyl ether (EGDE), polyethylene glycol monomethyl ether (mPEG), or any combination thereof. In some cases, the co-solvent can comprise an alcohol such as isopropyl alcohol (IPA), isobutyl alcohol (IBA), secondary butyl alcohol (SBA), or any combination thereof.

Aqueous Compositions

Also provided are aqueous surfactant compositions (also referred to as injection compositions) comprising a surfactant package described herein. These compositions can be used in oil and gas operations. These surfactant compositions can comprise water, an olefin sulfonate described herein, and one or more additional components chosen from one or more co-surfactants, a viscosity-modifying polymer, or any combination thereof.

The aqueous composition can be a low particle size injection fluid. In some embodiments, the surfactant package can be combined with an aqueous-based injection fluid to form a low particle size injection fluid prior to injection into a well. The surfactant package may be added directly into the aqueous-based injection fluid, or the surfactant package may be diluted (e.g., with water or an aqueous-based injection fluid) prior to being added to the injection fluid. In embodiments, the aqueous-based injection fluid prior to addition of the surfactant package is an aqueous-based injection fluid that was previously injected into the well. When added, the surfactant package can decrease the particle size distribution within the aqueous-based injection fluid, creating a low particle size injection fluid.

In example embodiments, the aqueous-based injection fluid can comprise any type of water, treated or untreated, and can vary in salt content. For example, the aqueous-based injection fluid can comprise sea water, brackish water, fresh water, flowback or produced water, wastewater (e.g., reclaimed or recycled), river water, lake or pond water, aquifer water, brine (e.g., reservoir or synthetic brine), or any combination thereof. In some embodiments, the aqueous-based injection fluid can comprise slickwater.

The low particle size injection fluids can comprise from 30% to 99.85% by weight of the total composition of water, for example from 70% to 98% water.

In some embodiments, the aqueous-based injection fluid can include an acid, a polymer, a friction reducer, a gelling agent, a crosslinker, a breaker, a pH adjusting agent, a non-emulsifier agent, an iron control agent, a scale inhibitor, a corrosion inhibitor, a biocide, a clay stabilizing agent, a proppant, a wettability alteration chemical, a co-solvent (e.g., a C1-C5 alcohol, or an alkoxylated C1-C5 alcohol), or any combination thereof. In certain embodiments, the aqueous-based injection fluid can comprise an acid (e.g., at least 10% acid, such as from 10% to 20% by weight acid). In certain embodiments, the injection fluid can comprise a proppant.

Once combined with the aqueous-based injection fluid, the primary surfactant can have a concentration within the low particle size injection fluid of at least 0.01% by weight (e.g., at least 0.02% by weight, at least 0.03% by weight, at least 0.04% by weight, at least 0.05% by weight, at least 0.06% by weight, at least 0.07% by weight, at least 0.08% by weight, at least 0.09% by weight, at least 0.1% by weight, at least 0.15% by weight, at least 0.2% by weight, at least 0.25% by weight, at least 0.3% by weight, at least 0.35% by weight, at least 0.4% by weight, at least 0.45% by weight, at least 0.5% by weight, at least 0.55% by weight, at least 0.6% by weight, at least 0.65% by weight, at least 0.7% by weight, at least 0.75% by weight, at least 0.8% by weight, at least 0.85% by weight, at least 0.9% by weight, at least 0.95% by weight, at least 1% by weight, at least 1.25% by weight, at least 1.5% by weight, at least 1.75% by weight, at least 2% by weight, or at least 2.25% by weight), based on the total weight of the low particle size injection fluid. In some embodiments, the primary surfactant can have a concentration within the low particle size injection fluid of 2.5% by weight or less (e.g., 2.25% by weight or less, 2% by weight or less, 1.75% by weight or less, 1.5% by weight or less, 1.25% by weight or less, 1% by weight or less, 0.95% by weight or less, 0.9% by weight or less, 0.85% by weight or less, 0.8% by weight or less, 0.75% by weight or less, 0.7% by weight or less, 0.65% by weight or less, 0.6% by weight or less, 0.55% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, or 0.02% by weight or less), based on the total weight of the LPS injection fluid. In particular embodiments, the primary surfactant can have a concentration within the low particle size injection fluid of less than 1%, less than 0.5%, less than 0.2%, less than 0.1%, less than 0.075%, or less than 0.05%.

The primary surfactant can have a concentration within the low particle size injection fluid ranging from any of the minimum values described above to any of the maximum values described above. For example, in some embodiments, the primary surfactant can have a concentration within the low particle size injection fluid of from 0.01% to 2.5% by weight (e.g., from 0.05% to 0.5% by weight), based on the total weight of the low particle size injection fluid.

When present, the one or more secondary surfactants can have a concentration within the low particle size injection fluid of at least 0.001% by weight (e.g., at least 0.005% by weight, at least 0.01% by weight, at least 0.02% by weight, at least 0.03% by weight, at least 0.04% by weight, at least 0.05% by weight, at least 0.06% by weight, at least 0.07% by weight, at least 0.08% by weight, at least 0.09% by weight, at least 0.1% by weight, at least 0.15% by weight, at least 0.2% by weight, at least 0.25% by weight, at least 0.3% by weight, at least 0.35% by weight, at least 0.4% by weight, at least 0.45% by weight, at least 0.5% by weight, at least 0.55% by weight, at least 0.6% by weight, at least 0.65% by weight, at least 0.7% by weight, at least 0.75% by weight, at least 0.8% by weight, at least 0.85% by weight, at least 0.9% by weight, at least 0.95% by weight, at least 1% by weight, at least 1.25% by weight, at least 1.5% by weight, at least 1.75% by weight, at least 2% by weight, or at least 2.25% by weight), based on the total weight of the low particle size injection fluid. In some embodiments, the one or more secondary surfactants can have a concentration within the low particle size injection fluid of 2.5% by weight or less (e.g., 2.25% by weight or less, 2% by weight or less, 1.75% by weight or less, 1.5% by weight or less, 1.25% by weight or less, 1% by weight or less, 0.95% by weight or less, 0.9% by weight or less, 0.85% by weight or less, 0.8% by weight or less, 0.75% by weight or less, 0.7% by weight or less, 0.65% by weight or less, 0.6% by weight or less, 0.55% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, 0.02% by weight or less, 0.01% by weight or less, or 0.005% by weight or less), based on the total weight of the LPS injection fluid. In particular embodiments, the one or more secondary surfactants can have a concentration within the low particle size injection fluid of less than 2%, less than 1.5%, less than 1%, less than 0.5%, less than 0.2%, less than 0.1%, less than 0.075%, less than 0.05%, or less than 0.01%.

When present, the one or more secondary surfactants can have a concentration within the low particle size injection fluid ranging from any of the minimum values described above to any of the maximum values described above. For example, in some embodiments, the one or more secondary surfactants can have a concentration within the low particle size injection fluid of from 0.001% to 2.5% by weight (e.g., from 0.001% to 1.5% by weight, or from 0.05% to 0.5% by weight), based on the total weight of the low particle size injection fluid.

In some embodiments, the primary surfactant and one or more secondary surfactants can be present in the LPS injection fluid, the single-phase liquid surfactant package, or both in a weight ratio of primary surfactant to one or more secondary surfactants of at least 1:1 (e.g., at least 2:1, at least 2.5:1, at least 3:1, at least 4:1, at least 5:1, at least 6:1, at least 7:1, at least 8:1, or at least 9:1). In some embodiments, the primary surfactant and one or more secondary surfactants can be present in the LPS injection fluid, the single-phase liquid surfactant package, or both in a weight ratio of primary surfactant to one or more secondary surfactants of 10:1 or less (e.g., 9:1 or less; 8:1 or less, 7:1 or less, 6:1 or less, 5:1 or less, 4:1 or less, 3:1 or less, 2.5:1 or less, or 2:1 or less).

The primary surfactant and one or more secondary surfactants can be present in the LPS injection fluid, the surfactant package, or both in a weight ratio ranging from any of the minimum values described above to any of the maximum values described above. For example, the primary surfactant and one or more secondary surfactants can be present in the LPS injection fluid, the surfactant package, or both in a weight ratio of primary surfactant to one or more secondary surfactants of from 1:1 to 10:1 (e.g., 1:1 to 5:1).

In other embodiments, the one or more secondary surfactants are absent (i.e., the primary surfactant is the only surfactant present in the surfactant package).

In some embodiments, the total concentration of all surfactants in the LPS injection fluid (the total concentration of the primary surfactant and the one or more secondary surfactants in the LPS injection fluid) can be at least 0.01% by weight (e.g., at least 0.02% by weight, at least 0.03% by weight, at least 0.04% by weight, at least 0.05% by weight, at least 0.06% by weight, at least 0.07% by weight, at least 0.08% by weight, at least 0.09% by weight, at least 0.1% by weight, at least 0.15% by weight, at least 0.2% by weight, at least 0.25% by weight, at least 0.3% by weight, at least 0.35% by weight, at least 0.4% by weight, at least 0.45% by weight, at least 0.5% by weight, at least 0.55% by weight, at least 0.6% by weight, at least 0.65% by weight, at least 0.7% by weight, at least 0.75% by weight, at least 0.8% by weight, at least 0.85% by weight, at least 0.9% by weight, at least 0.95% by weight, at least 1% by weight, at least 1.25% by weight, at least 1.5% by weight, at least 1.75% by weight, at least 2% by weight, at least 2.25% by weight, at least 2.5% by weight, at least 2.75% by weight, at least 3% by weight, at least 3.25% by weight, at least 3.5% by weight, at least 3.75% by weight, at least 4% by weight, at least 4.25% by weight, at least 4.5% by weight, or at least 4.75% by weight), based on the total weight of the LPS injection fluid. In some embodiments, the total concentration of all surfactants in the LPS injection fluid (the total concentration of the primary surfactant and the one or more secondary surfactants in the LPS injection fluid) can be 5% by weight or less (e.g., 4.75% by weight or less, 4.5% by weight or less, 4.25% by weight or less, 4% by weight or less, 3.75% by weight or less, 3.5% by weight or less, 3.25% by weight or less, 3% by weight or less, 2.75% by weight or less, 2.5% by weight or less, 2.25% by weight or less, 2% by weight or less, 1.75% by weight or less, 1.5% by weight or less, 1.25% by weight or less, 1% by weight or less, 0.95% by weight or less, 0.9% by weight or less, 0.85% by weight or less, 0.8% by weight or less, 0.75% by weight or less, 0.7% by weight or less, 0.65% by weight or less, 0.6% by weight or less, 0.55% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, or 0.02% by weight or less), based on the total weight of the LPS injection fluid.

The total concentration of all surfactants in the LPS injection fluid (the total concentration of the primary surfactant and the one or more secondary surfactants in the LPS injection fluid) can range from any of the minimum values described above to any of the maximum values described above. For example, in some embodiments, the total concentration of all surfactants in the LPS injection fluid (the total concentration of the primary surfactant and the one or more secondary surfactants in the LPS injection fluid) can be from 0.01% by weight to 5% by weight (e.g., from 0.01% to 2.5% by weight, from 0.01% to 1% by weight, or from 0.01% to 0.5% by weight).

In some embodiments when the LPS injection fluid is being injected into a horizontal well, the total concentration of all surfactants in the LPS injection fluid (the total concentration of the primary surfactant and the one or more secondary surfactants in the LPS injection fluid) can be from 0.01% to 1.5% by weight, from 0.01% to 1% by weight, or from 0.01% to 0.5% by weight).

In some embodiments when the LPS injection fluid is being injected into a vertical well, the total concentration of all surfactants in the LPS injection fluid (the total concentration of the primary surfactant and the one or more secondary surfactants in the LPS injection fluid) can be from 0.01% to 5% by weight, from 0.01% to 1% by weight, from 0.5% to 5% by weight, from 0.5% to 2.5% by weight, from 0.5% to 1.5% by weight, from 0.5% to 1% by weight, from 1% to 5% by weight, from 1% to 2.5% by weight, from or 1% to 1.5% by weight).

When present, the one or more co-solvents can have a concentration within the low particle size injection fluid of less than 2%, less than 1.5%, less than 1%, less than 0.5%, less than 0.2%, less than 0.1%, less than 0.075%, less than 0.05%, or less than 0.01%. For example, the one or more co-solvents can have a concentration within the low particle size injection fluid of from 0.001% to 1.5% by weight (e.g., 0.05% to 0.5% by weight), based on the total weight of the low particle size injection fluid.

After the surfactant package has been combined with the aqueous-based injection fluid, the LPS injection fluid may be a single-phase fluid or may be an emulsion depending on the amount of oil within the injection fluid.

In some embodiments, the primary surfactant and the one or more secondary surfactants can be added to the aqueous-based injection fluid to form the LPS injection fluid. For example, the primary surfactant and the one or more secondary surfactants can be pre-mixed as components of the surfactant package. Alternatively, the primary surfactant and the one or more secondary surfactants can be separately combined with (e.g., sequentially added to) the aqueous-based injection fluid to form the LPS injection fluid. In other embodiments, the primary surfactant and/or the one or more secondary surfactants can be added separately or together to an aqueous-based injection fluid when preparing slickwater in a tank. In some embodiments, the primary surfactant and the one or more secondary surfactants can be mixed with one or more additional components prior to combination with the aqueous-based injection fluid.

The one or more surfactants present in the surfactant package (and ultimately the LPS injection fluid) can be selected to improve hydrocarbon recovery. Specifically, the one or more surfactants can improve hydrocarbon recovery by increasing the aqueous stability of the LPS injection fluid at the temperature and salinity of the reservoir, decreasing the interfacial tension (IFT) of the LPS injection fluid with hydrocarbons in the reservoir, changing (e.g., increasing or decreasing the wettability of the reservoir, or any combination thereof.

In some embodiments, the one or more surfactants in the surfactant package (and ultimately the LPS injection fluid) can increase the aqueous stability of the LPS injection fluid at the temperature and salinity of the reservoir. Aqueous stable solutions can propagate further into a reservoir upon injection as compared to an injection fluid lacking aqueous stability. In addition, because injected chemicals remain soluble aqueous stable solutions, aqueous stable solutions do not precipitate particulates or phase separate within the formation which may obstruct or hinder fluid flow through the reservoir. As such, injection fluids that exhibit aqueous stability under reservoir conditions can largely eliminate formation damage associated with precipitation of injected chemicals. In this way, hydrocarbon recovery can be facilitated by the one or more surfactants in the surfactant package.

In some embodiments, the one or more surfactants in the surfactant package (and ultimately the LPS injection fluid) can decrease the interfacial tension (IFT) of the LPS injection fluid with hydrocarbons in the reservoir. Reducing the IFT can decrease pressure required to drive an aqueous-based injection fluid into the formation matrix. In addition, decreasing the IFT reduces water block during production, facilitating the flow of hydrocarbons from the formation to the wellbore (e.g., facilitating the flow of hydrocarbons back through the fractures and to the wellbore). In this way, hydrocarbon recovery can be facilitated by the one or more surfactants in the surfactant package.

In some embodiments, the one or more surfactants in the surfactant package (and ultimately the LPS injection fluid) can change the wettability of the reservoir. In particular, in embodiments where the reservoir is oil-wet or mixed-wet, the one or more surfactants in the surfactant package (and ultimately the LPS injection fluid) can make the reservoir more water-wet. By increasing the water-wetness of the reservoir, the formation will imbibe injected aqueous-based injection fluid into the formation matrix, leading to a corresponding flow of hydrocarbon from regions within the formation back to the fracture. In this way, hydrocarbon recovery can be facilitated by the one or more surfactants in the surfactant package.

In some embodiments, the one or more surfactants can improve hydrocarbon recovery by increasing the aqueous stability of the LPS injection fluid at the temperature and salinity of the reservoir and decreasing the interfacial tension (IFT) of the LPS injection fluid with hydrocarbons in the reservoir. In some embodiments, the one or more surfactants can improve hydrocarbon recovery by decreasing the interfacial tension (IFT) of the LPS injection fluid with hydrocarbons in the reservoir and increasing the wettability of the reservoir. In some embodiments, the one or more surfactants can improve hydrocarbon recovery by increasing the aqueous stability of the LPS injection fluid at the temperature and salinity of the reservoir and increasing the wettability of the reservoir. In certain embodiments, the one or more surfactants can improve hydrocarbon recovery by increasing the aqueous stability of the LPS injection fluid at the temperature and salinity of the reservoir, decreasing the interfacial tension (IFT) of the LPS injection fluid with hydrocarbons in the reservoir, and changing the wettability of the reservoir.

In an embodiment, the surfactant package is tested by determining the mean particle size distribution through dynamic light scattering. In specific embodiments, the mean particle size distribution of the aqueous-based injection fluid decreases after addition of the single-phase liquid surfactant package. In embodiments, the average diameter of particle size of the LPS injection fluid (aqueous-based injection fluid plus single-phase liquid surfactant package) is less than 0.1 micrometers. In an embodiment, when tested at the specific reservoir temperature and salinity, the average diameter of the LPS injection fluid is less than 0.1 micrometers. In specific embodiments, the average diameter in particle size distribution measurement of the LPS injection fluid is less than the average pore size of the unconventional reservoir rock matrix.

In some embodiments, the surfactant packages as described herein can be combined with one or more additional components to form a foamed composition.

In some embodiments, the foamed composition can comprise an acid. The acid can comprise any suitable acid known in the art. In some embodiments, the acid can comprise a strong acid, such as HCl. In other embodiments, the acid can comprise a weak acid, such as an organic acid.

In some embodiments, the foamed composition can have a pH of at least 2 (e.g., at least 2.5, at least 3, at least 3.5, at least 4, at least 4.5, at least 5, or at least 5.5). In some embodiments, the foamed composition can have a pH of 6 or less (e.g., 5.5 or less, 5 or less, 4.5 or less, 4 or less, 3.5 or less, 3 or less, or 2.5 or less).

The foamed composition can have a pH ranging from any of the minimum values described above to any of the maximum values described above. For example, in some embodiments, the foamed composition can have a pH of from 2 to 6 (e.g., from 2 to 5.5, from 2 to 4, or from 2 to 3).

In some embodiments, the foamed composition can comprise an alkali agent.

The term "alkali agent" is used herein according to its conventional meaning and includes basic, ionic salts of alkali metals or alkaline earth metals. Alkali agents as provided herein are typically capable of reacting with an unrefined petroleum acid (e.g., an acid in crude oil (reactive oil)) to form soap (a surfactant salt of a fatty acid) in situ. These in situ generated soaps serve as a source of surfactants capable of reducing the interfacial tension of hydrocarbons with an aqueous composition. Examples of suitable alkali agents include, but are not limited to, sodium hydroxide, potassium hydroxide, sodium carbonate, potassium carbonate, sodium silicate, sodium metaborate, and salts of EDTA (e.g., EDTA tetrasodium salt or EDTA tetrapotassium salt). In one embodiment, the alkali agent is NaOH. In other embodiments, the alkali agent is $Na_2CO_3$.

In some embodiments, the foamed composition can have a pH of at least 8 (e.g., at least 8.5, at least 9, at least 9.5, at least 10, at least 10.5, at least 11, or at least 11.5). In some embodiments, the foamed composition can have a pH of 12 or less (e.g., 11.5 or less, 11 or less, 10.5 or less, 10 or less, 9.5 or less, 9 or less, or 8.5 or less).

The foamed composition can have a pH ranging from any of the minimum values described above to any of the maximum values described above. For example, in some embodiments, the foamed composition can have a pH of from 8 to 12 (e.g., from 8.5 to 12, from 9 to 12, from 8.5 to 11.5, from 9 to 11.5, from 8.5 to 11, or from 9 to 11).

In some embodiments, the foamed composition can comprise a co-solvent. Suitable co-solvents include alcohols, such as lower carbon chain alcohols such as isopropyl alcohol, ethanol, n-propyl alcohol, n-butyl alcohol, sec-butyl alcohol, n-amyl alcohol, sec-amyl alcohol, n-hexyl alcohol, sec-hexyl alcohol and the like; alcohol ethers, polyalkylene alcohol ethers, polyalkylene glycols, poly(oxyalkylene)glycols, poly(oxyalkylene)glycol ethers, ethoxylated phenol, or any other common organic co-solvent or any combination of any two or more co-solvents. In one embodiment, the co-solvent can comprise alkyl ethoxylate (C1-C6)-XEO X=1-30-linear or branched. In some embodiments, the co-solvent can comprise ethylene glycol butyl ether (EGBE), diethylene glycol monobutyl ether (DGBE), triethylene glycol monobutyl ether (TEGBE), ethylene glycol dibutyl ether (EGDE), polyethylene glycol monomethyl ether (mPEG), or any combination thereof. In some embodiments, the co-solvent can be present in the foamed composition in an amount of from 0.1% to 25% by weight (e.g. from 0.1% to 10% by weight, or from 0.5% to 5% by weight) of the total weight of the foamed composition.

In some embodiments, the foamed composition can comprise a viscosity-modifying polymer. Examples of viscosity-modifying polymer are known in the art. Examples of suitable polymers include biopolymers such as polysaccharides. For example, polysaccharides can be xanthan gum, scleroglucan, guar gum, a mixture thereof (e.g., any modifications thereof such as a modified chain), etc. Indeed, the terminology "mixtures thereof" or "combinations thereof" can include "modifications thereof" herein. Examples of suitable synthetic polymers include polyacrylamides. Examples of suitable polymers include synthetic polymers such as partially hydrolyzed polyacrylamides (HPAMs or PHPAs) and hydrophobically-modified associative polymers (APs). Also included are co-polymers of polyacrylamide (PAM) and one or both of 2-acrylamido 2-methylpropane sulfonic acid (and/or sodium salt) commonly referred to as AMPS (also more generally known as acrylamido tertiobutyl sulfonic acid or ATBS), N-vinyl pyrrolidone (NVP), and the NVP-based synthetic may be single-, co-, or terpolymers. In one embodiment, the synthetic polymer is polyacrylic acid (PAA). In one embodiment, the synthetic polymer is polyvinyl alcohol (PVA). Copolymers may be made of any combination or mixture above, for example, a combination of NVP and ATBS. In certain embodiments, the viscosity-modifying polymer can comprise an uncrosslinked polymer. In some embodiments, the viscosity-modifying polymer can be present in the foamed composition in an amount of from 0.1% to 25% by weight (e.g. from 0.1% to 10% by weight, or from 0.5% to 5% by weight) of the total weight of the foamed composition.

In some embodiments, the foamed composition can further comprise a foam stabilizer. Foam stabilizers are known in the art and include, for example, crosslinkers, particulate stabilizers, or any combination thereof.

In some embodiments, the foamed composition can further include a crosslinker, such as a borate crosslinking agent, a Zr crosslinking agent, a Ti crosslinking agent, an Al crosslinking agent, an organic crosslinker, or any combination thereof. When present, the viscosity-modifying polymer and the crosslinker can be present in a weight ratio of from 20:1 to 100:1.

In some embodiments, the foamed composition can further include a particulate stabilizer (e.g., nanoparticles or microparticles). Examples of suitable nanoparticles and microparticles are known in the art, and include, for example, nickel oxide, alumina, silica (surface-modified), a silicate, iron oxide ($Fe_3O_4$), titanium oxide, impregnated nickel on alumina, synthetic clay, natural clay, iron zinc sulfide, magnetite, iron octanoate, or any combination thereof. Other examples of suitable nanoparticles are described, for example, in U.S. Pat. No. 10,266,750, which is hereby incorporated by reference in its entirety.

In some embodiments, the foamed composition can further comprise a breaker. In certain embodiments, the period of time in step (c) comprises a period of time effective to allow the foamed composition to break.

In another aspect, the surfactant packages as described herein can be formulated into injection compositions that further comprise a borate-acid buffer. In some embodiments, the composition can comprise a borate-acid buffer, a surfactant package, and water. In some embodiments, the composition can comprise a borate-acid buffer, a surfactant package, a polymer, and water.

The water used to form the aqueous injection compositions can comprise any type of water, treated or untreated, and can vary in salt content. For example, the water can comprise sea water, brackish water, fresh water, flowback or produced water, wastewater (e.g., reclaimed or recycled), river water, lake or pond water, aquifer water, brine (e.g., reservoir or synthetic brine), or any combination thereof.

In some embodiments, the water can comprise hard water or hard brine. The hard water or hard brine comprises a divalent metal ion chosen from $Ca^{2+}$, $Mg^{2+}$, $Sr^{2+}$, $Ba^{2+}$, or any combination thereof. In certain embodiments, the hard water or hard brine can comprise at least 10 ppm at least 100 ppm, at least 500 ppm, at least 1,000 ppm, at least 5,000 ppm, or at least 10,000 ppm of divalent metal ions chosen from $Ca^{2+}$, $Mg^{2+}$, $Sr^{2+}$, $Ba^{2+}$, or any combination thereof. In certain examples, the hard water or hard brine can comprise from 100 ppm to 25,000 ppm of divalent metal ions chosen from $Ca^{2+}$, $Mg^{2+}$, $Sr^{2+}$, $Ba^{2+}$, or any combination thereof.

The borate-acid buffer serves to buffer the pH of the injection composition. The composition can be buffered such that a minimal addition of an acid or base to the buffered composition will not substantially impact the pH of the composition. In some embodiments, the borate-acid buffer can exhibit a capacity to buffer at a pH of from at least 6 (e.g., a pH of at least 6.25, a pH of at least 6.5, a pH of at least 6.75, a pH of at least 7, a pH of at least 7.25, a pH of at least 7.5, a pH of at least 7.75, a pH of at least 8, or a pH of at least 8.25). In some embodiments, the borate-acid buffer can exhibit a capacity to buffer at a pH of 8.5 or less (e.g., a pH of 8.25 or less, a pH of 8 or less, a pH of 7.75 or less, a pH of 7.5 or less, a pH of 7.25 or less, a pH of 7 or less, a pH of 6.75 or less, a pH of 6.5 or less, or a pH of 6.25 or less).

The borate-acid buffer can exhibit a capacity to buffer at a pH ranging from any of the minimum values described above to any of the maximum values described above. For example, the borate-acid buffer can exhibit a capacity to buffer at a pH of from 6 to 8.5 (e.g., from 6.5 to 7.5, from 6 to 7.5, from 6.5 to 7, or from 6 to 7).

In certain embodiments, the borate-acid buffer can exhibit a capacity to buffer at a pH of less than 8. In certain embodiments, the borate-acid buffer can exhibit a capacity to buffer at a pH of less than 7.

In some cases, the borate-acid buffer can exhibit a capacity to buffer at a pH below the point of zero charge of a formation into which the composition will be injected as part of an oil and gas operation.

In some embodiments, the injection composition can have a salinity of at least 5,000 ppm. In other embodiments, the injection composition has a salinity of at least 50,000 ppm. In other embodiments, the injection composition has a salinity of at least 100,000 ppm. In other embodiments, the injection composition has a salinity of at least 250,000 ppm. The total range of salinity (total dissolved solids in the brine) is 100 ppm to saturated brine (about 260,000 ppm).

In some embodiments, the injection composition can have a temperature of at least 20° C. (e.g., at least 30° C., at least 40° C., at least 50° C., at least 60° C., at least 70° C., at least 80° C., at least 90° C., at least 100° C., or at least 110° C.). The injection composition can have a temperature of 120° C. or less (e.g., 110° C. or less, 100° C. or less, 90° C. or less, 80° C. or less, 70° C. or less, 60° C. or less, 50° C. or less, 40° C. or less, or 30° C. or less). In some embodiments, the injection composition can have a temperature of greater than 120° C.

The injection composition can have a temperature ranging from any of the minimum values described above to any of the maximum values described above. For example, the injection composition can have a temperature of from 20° C. to 120° C. (e.g., from 50° C. to 120° C., or from 80° C. to 120° C.).

In some embodiments, the injection composition can have a viscosity of between 20 mPas and 100 mPas at 20° C. The viscosity of the injection solution may be increased from 0.3 mPas to 1, 2, 10, 20, 100 or even 1000 mPas by including a water-soluble polymer. The apparent viscosity of the injection composition may be increased with a gas (e.g., a foam forming gas) as an alternative to the water-soluble polymer.

The injection compositions described herein can include a borate-acid buffer.

In some embodiments, the borate-acid buffer can comprise a borate compound and a conjugate base of an acid.

A variety of suitable boron compounds may be used. Examples of boron compounds include Borax, Sodium tetraborate decahydrate ($Na_2B_4O_7 \cdot 10H_2O$), Borax pentahydrate ($Na_2B_4O_7 \cdot 5H_2O$), Kernite ($Na_2B_4O_7 \cdot 4H_2O$), Borax monohydrate ($Na_2O \cdot 2B_2O_3 \cdot H_2O$), Sodium metaborate tetrahydrate ($NaBO_2 \cdot 4H_2O$ or $Na_2O \cdot B_2O_3 \cdot 8H_2O$), Sodium metaborate dihydrate ($NaBO_2 \cdot 2H_2O$ or $Na_2O \cdot B_2O_3 \cdot 4H_2O$), Ezcurrite ($2Na_2O \cdot 5.1B_2O_3 \cdot 7H_2O$), Auger's sodium borate/Nasinite ($2Na_2O \cdot 5B_2O_3 \cdot 5H_2O$), Sodium pentaborate ($Na_2O \cdot 5B_2O_3 \cdot 10H_2O$), Potassium metaborate ($K_2O \cdot B_2O_3 \cdot 2.5H_2O$), Potassium tetraborate ($K_2O \cdot 2B_2O_3 \cdot 8H_2O$ or $4H_2O$), Auger's potassium pentaborate ($2K_2O \cdot 5B_2O_3 \cdot 5H_2O$), Potassium pentaborate ($K_2O \cdot 5B_2O_3 \cdot 8H_2O$), Lithium metaborate octahydrate ($LiBO_2 \cdot 8H_2O$ or $Li_2O \cdot B_2O_3 \cdot 16H_2O$), Lithium tetraborate trihydrate ($Li_2O \cdot 2B_2O_3 \cdot 3H_2O$), Lithium pentaborate ($Li_2O \cdot 5B_2O_3 \cdot 10H_2O$), Rubidium diborate ($Rb_2O \cdot 2B_2O_3 \cdot 5H_2O$), Rubidium pentaborate ($Rb_2O \cdot 5B_2O_3 \cdot 8H_2O$), Rubidium metaborate ($Rb_2O \cdot B_2O_3 \cdot 3H_2O$), Cesium Metaborate ($Cs_2O \cdot B_2O_3 \cdot 7H_2O$), Cesium diborate ($Cs_2O \cdot 2B_2O_3 \cdot 5H_2O$), Cesium pentaborate ($Cs_2O \cdot 5B_2O_3 \cdot 8H_2O$), Ammonium biborate (($NH_4)_2 \cdot 2B_2O_3 \cdot 4H_2O$), Ammonium pentaborate (($NH_4)_2O \cdot 5B_2O_3 \cdot 8H_2O$), Larderellite, probably (($NH_4)_2O \cdot 5B_2O_3 \cdot 4H_2O$), Ammonioborite (($NH_4)_2O \cdot 5B_2O_3 \cdot 5\frac{1}{3}H_2O$), Kernite (Rasorite) ($Na_2B_4O_2 \cdot 4H_2O$), Tincalconite (Mohavite) ($Na_2B_4O_7 \cdot 5H_2O$), Borax (Tincal) ($Na_2B_4O_7 \cdot 10H_2O$), Sborgite ($Na_2B_{10}O_{16} \cdot 10H_2O$), Ezcurrite ($Na_4B_{10}O_{17} \cdot 7H_2O$), Probertite (Kramerite) ($NaCaB_5O_9 \cdot 5H_2O$), Ulxiete (Hayesine, Franklandite) ($NaCaB_5O_9 \cdot 8H_2O$), Nobleite ($CaB_6O_{10} \cdot 4H_2O$), Gowerite ($CaB_6O_{10} \cdot 5H_2O$), Frolovite ($Ca_2B_4O_8 \cdot 7H_2O$), Colemanite ($Ca_2B_6O_{11} \cdot 5H_2O$), Meyerhofferite ($Ca_2B_6O_{11} \cdot 7H_2O$), Inyoite ($Ca_2B_6O_{11} \cdot 13H_2O$), Priceite {(Pandermite) (Cryptomorphite)} ($Ca_4B_{10}O_{19} \cdot 7H_2O$), Tertschite ($Ca_4B_{10}O_{19} \cdot 20H_2O$), Ginorite ($Ca_2B_{14}O_{23} \cdot 8H_2O$), Pinnoite ($MgB_2O_4 \cdot 3H_2O$), Paternoite ($MgB_8O_{13} \cdot 4H_2O$), Kurnakovite ($Mg_2B_6O_{11} \cdot 15H_2O$), Inderite (lesserite) (monoclinic) ($Mg_2B_6O_{11} \cdot 15H_2O$), Preobrazhenskite ($Mg_3B_{10}O_{18} \cdot 4\frac{1}{2}H_2O$), Hydroboracite ($CaMgB_6O_{11} \cdot 6H_2O$), Inderborite ($CaMgB_6O_{11} \cdot 11H_2O$), Kaliborite (Heintzite) ($KMg_2B_{11}O_{19} \cdot 9H_2O$), Larderellite (($NH_4)_2B_{10}O_{16} \cdot 4H_2O$), Ammonioborite (($NH_4)_2B_{10}O_{16}5\frac{1}{3}H_2O$), Veatchite ($SrB_6O_{10} \cdot 2H_2O$), p-Veatchite (($Sr,Ca)B_6O_{10} \cdot 2H_2O$), Teepleite ($Na_2B_2O_4 \cdot 2Na_2Cl.4H_2O$), Bandylite ($CuB_2O_4 \cdot CuCl_2 \cdot 4H_2O$), Hilgardite (monocline) ($3Ca_2B_6O_{11} \cdot 2CaCl_2 \cdot 4H_2O$), Parahilgardite (triclinic) ($3Ca_2B_6O_{11} \cdot 2CaCl_2 \cdot 4H_2O$), Boracite ($Mg_5B_{14}O_{26}MgCl_2$), Fluoborite ($Mg_3(BO_3)(F,OH)_3$), Hambergite ($Be_2(BO_3)(OH)$), Sussexite (($Mn,Zn)(BO_2)(OH)$), (Ascharite Camsellite) ($Mg(BO_2)(OH)$), Szaibelyite ($Mg(BO_2)(OH)$), Roweite (($Mn,Mg,Zn)Ca(BO_2)_2(OH)_2$), Seamanite ($Mn_3(PO_4)(BO_3).3H_2O$), Wiserite ($Mn_4B_2O_5(OH,Cl)_4$), Luneburgite ($Mg_3B_2(OH)_6(PO_4)_2 \cdot 6H_2O$), Cahnite ($Ca_2B(OH)_4(AsO_4)$), Sulfoborite ($Mg_6H_4(BO_3)_4(SO_4)_2 \cdot 7H_2O$), Johachidolite ($H_6Na_2Ca_3Al_4F_5B_6O_{20}$), Boric Acid, Sassolite ($H_3BO_3$), Jeremejewite (Eichwaldite) ($AlBO_3$), Kotoite ($Mg_3(BO_3)_2$), Nordenskioldine ($CaSn(BO_3)_2$), Rhodizite, Warwickite (($Mg,Fe)_3TiB_2O_6$), Ludwigite (Ferro-ludwegite, Vonsenite) (($Mg,Fe^{II})_2Fe^{III}BO_5$), Paigeite (($Fe^{II},Mg)_2Fe^{III}BO_5$), Pinakiolite ($Mg_3Mn^{II}Mn_2^{III}B_2O_{10}$), Axinite ($2Al_2O_3 \cdot 2(Fe,Mn)O \cdot 4CaO \cdot H_2O \cdot B_2O_38SiO_2$), Bakerite, Danburite ($CaO \cdot B_2O_3 \cdot 2SiO_2$), Datolite ($2CaO \cdot H_2O \cdot B_2O_3 \cdot SiO_2$), Dumortierite ($8Al_2O_3 \cdot H_2OB_2O_3 \cdot 6SiO_2$), Grandidierite ($11(Al,Fe,B)_2O_3 \cdot 7(Mg,Fe,Ca)O \cdot 2(H,Na,K)_2O \cdot 7SiO_2$), Homilite ($2CaO.FeO \cdot B_2O_3 \cdot 2SiO_2$), Howlite ($4CaO \cdot 5H_2O \cdot 5B_2O_3 \cdot 2SiO_2$), Hyalotekite ($16(Pb,Ba,Ca)O \cdot F \cdot 2B_2O_3 \cdot 24H_2O$), Kornerupine, Manandonite ($7Al_2O_3 \cdot 2Li_2O \cdot 12H_2O \cdot 2B_2O_3 \cdot 6SiO_2$), Sapphirine, Searlesite ($Na_2O \cdot 2H_2O \cdot B_2O_3 \cdot 4SiO_2$), Serendibite ($3Al_2O_3 \cdot 2Ca \cdot 4MgO \cdot B_2O_3 \cdot 4SiO_2$), and any combination thereof.

In certain embodiments, in boron compound can comprise a metaborate or a borax. In certain embodiments, the boron compound can comprise sodium tetraborate, calcium tetraborate, sodium borate, sodium metaborate, or any combination thereof. In embodiments, the boron compound comprises sodium metaborate. The term "sodium metaborate" as provided herein refers to the borate salt having the chemical formula $NaBO_2 4H_2O$ and in the customary sense, refers to CAS Registry No. 10555-76-7. In embodiments, the boron compound comprises borax. Other suitable compounds include, for example, barium borate or zinc borate.

The acid can comprise any suitable acid. For example, the acid can comprise acetic acid, citric acid, boric acid, tartaric acid, hydrochloric acid, succinic acid, or any combination thereof. In some embodiments, the acid can comprise an organic acid. In some embodiment, the conjugate base of the acid comprises a chelator for a divalent metal ion (e.g., $Mg^{2+}$ or $Ca^{2+}$).

In some embodiments, the conjugate base of the acid comprises two or more heteroatoms (e.g., two or more oxygen atoms). In certain embodiments, the conjugate base comprises one or more carboxylate moieties. For example, the conjugate base can comprise acetate, citrate, tartrate, succinate, or any combination thereof.

The borate compound and the conjugate base of the organic acid can be present at a weight ratio of from 1:1 to 5:1 (e.g., from 1:1 to 3:1).

In some embodiments, the borate-acid buffer can comprise two or more different borate compounds, two or more conjugate bases of different acids, or any combination thereof. By way of illustration, the borate-acid buffer can be prepared by mixing two or more borate compounds with an acid, a borate compound with two or more acids, or two or more borate compounds with two or more acids.

In some embodiments, the borate-acid buffer comprises a borate compound, a conjugate base of a first acid, and a conjugate base of a second acid. In some cases, the first acid comprises acetic acid. In some cases, the second acid comprises an acid whose conjugate base has lower solubility in the aqueous composition than acetate. For example, the second acid can comprise citric acid.

In some embodiments, the borate-acid buffer can comprise a first borate compound, second borate compounds, and a conjugate base of an acid.

One of ordinary skill in the art will recognize that the borate-acid buffers described above can likewise be formed by combining boric acid with an alkali.

For example, borate-acid buffers can be formed by combining boric acid an alkali such as an acetate salt (e.g., sodium acetate, potassium acetate), a citrate salt (e.g., sodium citrate, potassium citrate), a tartrate salt (e.g., sodium tartrate, potassium tartrate, sodium potassium tartrate, potassium bitartrate), a hydroxide salt (e.g., sodium hydroxide, potassium hydroxide), a succinate salt (e.g., sodium succinate, potassium succinate), or any combination thereof.

In these examples, the alkali can form a conjugate acid that comprises a chelator for a divalent metal ion. In some cases, the conjugate acid can comprise two or more heteroatoms (e.g., two or more oxygen atoms). In certain cases, the conjugate acid can comprise one or more carboxylate moieties.

The borate-acid buffer can have a concentration within the injection composition of at least 0.01% by weight (e.g., at least 0.02% by weight, at least 0.03% by weight, at least 0.04% by weight, at least 0.05% by weight, at least 0.06% by weight, at least 0.07% by weight, at least 0.08% by weight, at least 0.09% by weight, at least 0.1% by weight, at least 0.15% by weight, at least 0.2% by weight, at least 0.25% by weight, at least 0.3% by weight, at least 0.35% by weight, at least 0.4% by weight, at least 0.45% by weight, at least 0.5% by weight, at least 0.55% by weight, at least 0.6% by weight, at least 0.65% by weight, at least 0.7% by weight, at least 0.75% by weight, at least 0.8% by weight, at least 0.85% by weight, at least 0.9% by weight, at least 0.95% by weight, at least 1% by weight, at least 1.25% by weight, at least 1.5% by weight, at least 1.75% by weight, at least 2% by weight, at least 2.5% by weight, at least 3% by weight, at least 3.5% by weight, at least 4% by weight, or at least 4.5% by weight), based on the total weight of the injection composition. In some embodiments, the borate-acid buffer can have a concentration within the injection composition of 5% by weight or less (e.g., 4.5% by weight or less, 4% by weight or less, 3.5% by weight or less, 3% by weight or less, 2.5% by weight or less, 2% by weight or less, 1.75% by weight or less, 1.5% by weight or less, 1.25% by weight or less, 1% by weight or less, 0.95% by weight or less, 0.9% by weight or less, 0.85% by weight or less, 0.8% by weight or less, 0.75% by weight or less, 0.7% by weight or less, 0.65% by weight or less, 0.6% by weight or less, 0.55% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, or 0.02% by weight or less), based on the total weight of the injection composition.

The borate-acid buffer can have a concentration within the injection composition ranging from any of the minimum values described above to any of the maximum values described above. For example, in some embodiments, the borate-acid buffer can have a concentration within the injection composition of from 0.01% to 5% by weight (e.g., from 0.01% to 2.5% by weight, from 0.01% to 2% by weight, from 0.05% to 5% by weight, from 0.05% to 2.5% by weight, from 0.05% to 1% by weight, or from 0.05% to 0.5% by weight), based on the total weight of the injection composition.

In some embodiments, the injection compositions can further include a polymer, such as a viscosity enhancing water-soluble polymer. In some embodiments, the water-soluble polymer may be a biopolymer such as xanthan gum or scleroglucan, a synthetic polymer such as polyacryamide, hydrolyzed polyarcrylamide or co-polymers of acrylamide and acrylic acid, 2-acrylamido 2-methyl propane sulfonate or N-vinyl pyrrolidone, a synthetic polymer such as polyethylene oxide, or any other high molecular weight polymer soluble in water or brine. In some embodiments, the polymer is polyacrylamide (PAM), partially hydrolyzed polyacrylamides (HPAM), and copolymers of 2-acrylamido-2-methylpropane sulfonic acid or sodium salt or mixtures thereof, and polyacrylamide (PAM) commonly referred to as AMPS copolymer and mixtures of the copolymers thereof. In one embodiment, the viscosity enhancing water-soluble polymer is polyacrylamide or a co-polymer of polyacrylamide. In one embodiment, the viscosity enhancing water-soluble polymer is a partially (e.g. 20%, 25%, 30%, 35%, 40%, 45%) hydrolyzed anionic polyacrylamide. Molecular weights of the polymers may range from about 10,000 Daltons to about 20,000,000 Daltons. In some embodiments, the viscosity enhancing water-soluble polymer is used in the range of about 100 to about 5000 ppm concentration, such as from about 1000 to 2000 ppm (e.g., in order to match or exceed the reservoir oil viscosity under the reservoir conditions of temperature and pressure). The polymer can be a powder polymer, a liquid polymer, or an emulsion polymer.

Some examples of polymers are discussed in the following: U.S. Pat. Nos. 9,909,053, 9,896,617, 9,902,894, 9,902,895, U.S. Patent Application Publication No. 2017/0158947, U.S. Patent Application Publication No. 2017/0158948, and U.S. Patent Application Publication No. 2018/0155505, each of which is incorporated by reference in its entirety. More examples of polymers may be found in Dwarakanath et al., "Permeability Reduction Due to use of Liquid Polymers and Development of Remediation Options," SPE 179657, SPE IOR Symposium in Tulsa, 2016, which is incorporated by reference in its entirety.

In some embodiments, the injection compositions can further include a co-solvent. Suitable co-solvents include alcohols, such as lower carbon chain alcohols such as isopropyl alcohol, ethanol, n-propyl alcohol, n-butyl alcohol, sec-butyl alcohol, n-amyl alcohol, sec-amyl alcohol, n-hexyl alcohol, sec-hexyl alcohol and the like; alcohol ethers, polyalkylene alcohol ethers, polyalkylene glycols, poly(oxyalkylene)glycols, poly(oxyalkylene)glycol ethers, ethoxylated phenol, or any other common organic co-solvent or any combination of any two or more co-solvents. In one embodiment, the co-solvent can comprise alkyl ethoxylate (C1-C6)-XEO X=1-30-linear or branched. In some embodiments, the co-solvent can comprise ethylene glycol butyl ether (EGBE), diethylene glycol monobutyl ether (DGBE), triethylene glycol monobutyl ether (TEGBE), ethylene glycol dibutyl ether (EGDE), polyethylene glycol monomethyl ether (mPEG), or any combination thereof.

The injection compositions provided herein may include more than one co-solvent. Thus, in embodiments, the injection composition includes a plurality of different co-solvents. Where the injection composition includes a plurality of different co-solvents, the different co-solvents can be distinguished by their chemical (structural) properties. For example, the injection composition may include a first co-solvent, a second co-solvent and a third co-solvent, wherein the first co-solvent is chemically different from the second and the third co-solvent, and the second co-solvent is chemically different from the third co-solvent. In embodiments, the plurality of different co-solvents includes at least two different alcohols (e.g., a $C_1$-$C_6$ alcohol and a $C_1$-$C_4$ alcohol). In embodiments, the aqueous composition includes a $C_1$-$C_6$ alcohol and a $C_1$-$C_4$ alcohol. In embodiments, the plurality of different co-solvents includes at least two different alkoxy alcohols (e.g., a $C_1$-$C_6$ alkoxy alcohol and a $C_1$-$C_4$ alkoxy alcohol). In embodiments, the injection composition includes a $C_1$-$C_6$ alkoxy alcohol and a $C_1$-$C_4$ alkoxy alcohol. In embodiments, the plurality of different co-solvents includes at least two co-solvents selected from the group consisting of alcohols, alkyl alkoxy alcohols and phenyl alkoxy alcohols. For example, the plurality of different co-solvents may include an alcohol and an alkyl alkoxy alcohol, an alcohol and a phenyl alkoxy alcohol, or an alcohol, an alkyl alkoxy alcohol and a phenyl alkoxy alcohol. The alkyl alkoxy alcohols or phenyl alkoxy alcohols provided herein have a hydrophobic portion (alkyl or aryl chain), a hydrophilic portion (e.g., an alcohol) and optionally an alkoxy (ethoxylate or propoxylate) portion. Thus, in embodiments, the co-solvent is an alcohol, alkoxy alcohol, glycol ether, glycol or glycerol. Suitable co-solvents are known in the art, and include, for example, co-surfactants described in U.S. Patent Application Publication No. 2013/0281327 which is hereby incorporated herein in its entirety.

The co-solvents can have a concentration within the injection composition of at least 0.01% by weight (e.g., at least 0.02% by weight, at least 0.03% by weight, at least 0.04% by weight, at least 0.05% by weight, at least 0.06% by weight, at least 0.07% by weight, at least 0.08% by weight, at least 0.09% by weight, at least 0.1% by weight, at least 0.15% by weight, at least 0.2% by weight, at least 0.25% by weight, at least 0.3% by weight, at least 0.35% by weight, at least 0.4% by weight, at least 0.45% by weight, at least 0.5% by weight, at least 0.55% by weight, at least 0.6% by weight, at least 0.65% by weight, at least 0.7% by weight, at least 0.75% by weight, at least 0.8% by weight, at least 0.85% by weight, at least 0.9% by weight, at least 0.95% by weight, at least 1% by weight, at least 1.25% by weight, at least 1.5% by weight, at least 1.75% by weight, at least 2% by weight, at least 2.5% by weight, at least 3% by weight, at least 3.5% by weight, at least 4% by weight, or at least 4.5% by weight), based on the total weight of the aqueous composition. In some embodiments, the co-solvents can have a concentration within the aqueous composition of 5% by weight or less (e.g., 4.5% by weight or less, 4% by weight or less, 3.5% by weight or less, 3% by weight or less, 2.5% by weight or less, 2% by weight or less, 1.75% by weight or less, 1.5% by weight or less, 1.25% by weight or less, 1% by weight or less, 0.95% by weight or less, 0.9% by weight or less, 0.85% by weight or less, 0.8% by weight or less, 0.75% by weight or less, 0.7% by weight or less, 0.65% by weight or less, 0.6% by weight or less, 0.55% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, or 0.02% by weight or less), based on the total weight of the injection composition.

The co-solvents can have a concentration within the injection composition ranging from any of the minimum values described above to any of the maximum values described above. For example, in some embodiments, the co-solvents can have a concentration within the injection composition of from 0.01% to 5% by weight (e.g., from 0.01% to 2.5% by weight, from 0.05% to 5% by weight, from 0.05% to 2.5% by weight, from 0.05% to 1% by weight, or from 0.05% to 0.5% by weight), based on the total weight of the injection composition.

Optionally, the injection composition can further comprise additional components for use in oil and gas operations, such as a friction reducer, a gelling agent, a cross-linker, a breaker, a pH adjusting agent, a non-emulsifier agent, an iron control agent, a corrosion inhibitor, a scale inhibitor, a biocide, a clay stabilizing agent, a chelating agent, a proppant, a wettability alteration chemical, or any combination thereof.

In some embodiments, the injection composition can further include a gas. For instance, the gas may be combined with the aqueous composition to reduce its mobility by decreasing the liquid flow in the pores of the solid material (e.g., rock). In some embodiments, the gas may be supercritical carbon dioxide, nitrogen, natural gas or mixtures of these and other gases.

In some embodiments, the surfactant package (and by extension the aqueous composition) can comprise a non-ionic surfactant and an anionic surfactant (e.g., an olefin sulfonate described herein and/or disulfonate). In some embodiments, the surfactant package (and by extension the aqueous composition) can comprise a non-ionic surfactant and two or more anionic surfactants (e.g., an olefin sulfonate described herein and/or disulfonate and/or a carboxylate). In some embodiments, the surfactant package (and by extension the aqueous composition) can comprise a non-ionic surfactant (e.g., a C6-C16 alkyl phenol ethoxylate, or a C6-C16:PO(0-25):EO(0-25), such as a C9-C11 ethoxylated alcohol, a C13 ethoxylated alcohol, a C6-C10 ethoxylated propoxylated alcohol, or a C10-C14 ethoxylated Guerbet alcohol) and a sulfonate surfactant (e.g., a C10-16 disulfonate, and/or an olefin sulfonate described herein). In some embodiments, the surfactant package (and by extension the aqueous composition) can comprise a non-ionic surfactant (e.g., a C6-C16 alkyl phenol ethoxylate, or a C6-16:PO(0-25):EO(0-25), such as a C9-C11 ethoxylated alcohol, a C13 ethoxylated alcohol, a C6-C10 ethoxylated propoxylated alcohol, or a C10-C14 ethoxylated Guerbet alcohol), a sulfonate surfactant (e.g., a C10-16 disulfonate, and/or an olefin sulfonate described herein), and a carboxylate surfactant (e.g., a C10-16 alkyl polyglucoside carboxylate or a C22-C36 Guerbet alkoxylated carboxylate).

Specific example embodiments include aqueous compositions comprising the surfactant packages (and in some cases co-solvents) in the table below.

| Example | Surfactants and Co-Solvents in Aqueous Composition (in weight percent) |
|---|---|
| 1 | 0.15% alkoxylated C6-C16 alcohol<br>0.05% carboxylate<br>0.05% olefin sulfonate<br>0.05% alkyl polyglucoside |
| 2 | 0.1% alkoxylated C6-C16 alcohol<br>0.05% carboxylate<br>0.05% olefin sulfonate<br>0.1% alkyl polyglucoside |
| 3 | 0.15% alkoxylated C6-C16 alcohol<br>0.07% carboxylate<br>0.03% olefin sulfonate<br>0.1% alkyl polyglucoside |
| 4 | 0.1% alkoxylated C6-C16 alcohol<br>0.04% carboxylate<br>0.05% olefin sulfonate<br>0.03% disulfonate<br>0.1% alkyl polyglucoside |
| 5 | 0.15% alkoxylated C6-C16 alcohol<br>0.15% alkoxylated alkylphenol<br>0.1% olefin sulfonate<br>0.1% Guerbet alkoxylated carboxylate |
| 6 | 0.125% alkoxylated C6-C16 alcohol<br>0.175% alkoxylated alkylphenol<br>0.1% olefin sulfonate<br>0.1% Guerbet alkoxylated carboxylate |
| 7 | 0.1% alkoxylated C6-C16 alcohol<br>0.2% alkoxylated alkylphenol<br>0.1% olefin sulfonate<br>0.1% Guerbet alkoxylated carboxylate |
| 8 | 0.12% alkoxylated C6-C16 alcohol<br>0.22% alkoxylated alkylphenol<br>0.08% olefin sulfonate<br>0.08% Guerbet alkoxylated carboxylate |
| 9 | 0.15% alkoxylated C6-C16 alcohol<br>0.15% alkoxylated alkylphenol<br>0.08% olefin sulfonate<br>0.06% Guerbet alkoxylated carboxylate<br>0.06% carboxylate |
| 10 | 0.15% alkoxylated C6-C16 alcohol<br>0.15% alkoxylated alkylphenol<br>0.05% olefin sulfonate<br>0.1% Guerbet alkoxylated carboxylate<br>0.05% disulfonate |
| 11 | 0.5% olefin sulfonate<br>0.5% Guerbet alkoxylated carboxylate<br>0.55% glycosides or glucosides |
| 12 | 0.5% olefin sulfonate<br>0.5% Guerbet alkoxylated carboxylate<br>0.5% glycosides or glucosides<br>0.25% alkoxylated C6-C16 alcohol |
| 13 | 0.5% olefin sulfonate<br>0.5% Guerbet alkoxylated carboxylate<br>0.5% glycosides or glucosides<br>0.5% alkoxylated C6-C16 alcohol |
| 14 | 0.5% olefin sulfonate<br>0.5% Guerbet alkoxylated carboxylate<br>1% glycosides or glucosides<br>0.5% alkoxylated C6-C16 alcohol |
| 15 | 0.05% olefin sulfonate<br>0.05% Guerbet alkoxylated carboxylate<br>0.05% glycosides or glucosides<br>0.05% alkoxylated C6-C16 alcohol |
| 16 | 0.03% olefin sulfonate<br>0.04% Guerbet alkoxylated carboxylate<br>0.08% glycosides or glucosides<br>0.05% alkoxylated C6-C16 alcohol |
| 17 | 0.4% olefin sulfonate<br>0.4% Guerbet alkoxylated carboxylate<br>0.7% glycosides or glucosides<br>0.5% alkoxylated C6-C16 alcohol |
| 18 | 0.05% olefin sulfonate<br>0.1% glycosides or glucosides<br>0.05% alkoxylated C6-C16 alcohol |
| 19 | 0.05% olefin sulfonate<br>0.1% alkyl polyglucoside<br>0.05% alkoxylated C6-C16 alcohol |
| 20 | 0.05% olefin sulfonate<br>0.1% glycosides or glucosides<br>0.05% alkoxylated C6-C16 alcohol |
| 21 | 0.05% olefin sulfonate<br>0.1% alkyl polyglucoside<br>0.05% alkoxylated C6-C16 alcohol |
| 22 | 0.05% olefin sulfonate<br>0.1% alkyl polyglucoside<br>0.05% alkoxylated C6-C16 alcohol |
| 23 | 0.05% olefin sulfonate<br>0.05% glycosides or glucosides<br>0.05% alkoxylated C6-C16 alcohol<br>0.05% carboxylate |
| 24 | 0.05% olefin sulfonate<br>0.05% glycosides or glucosides<br>0.05% alkoxylated C6-C16 alcohol<br>0.05% carboxylate |
| 25 | 0.05% olefin sulfonate<br>0.05% alkyl polyglucoside<br>0.05% alkoxylated C6-C16 alcohol |
| 26 | 0.06% olefin sulfonate<br>0.05% alkyl polyglucoside<br>0.04% alkoxylated C6-C16 alcohol |
| 27 | 0.04% olefin sulfonate<br>0.08% glycosides or glucosides<br>0.05% alkoxylated C6-C16 alcohol<br>0.03% disulfonate |
| 28 | 0.035% olefin sulfonate<br>0.075% glycosides or glucosides<br>0.05% alkoxylated C6-C16 alcohol<br>0.04% disulfonate |
| 29 | 0.035% olefin sulfonate<br>0.07% glycosides or glucosides<br>0.045% alkoxylated C6-C16 alcohol<br>0.05% disulfonate |

-continued

| Example | Surfactants and Co-Solvents in Aqueous Composition (in weight percent) |
|---|---|
| 30 | 0.25% Guerbet alkoxylated carboxylate<br>0.25% olefin sulfonate<br>0.5% glycosides or glucosides<br>0.5% co-solvent |
| 31 | 0.25% olefin sulfonate<br>1.0% alkoxylated C6-C16 alcohol |
| 32 | 0.15% olefin sulfonate<br>0.2% Guerbet alkoxylated carboxylate<br>0.92% carboxylate |
| 33 | 0.65% carboxylate<br>0.35% alkoxylated C6-C16 alcohol<br>1% olefin sulfonate |
| 34 | 1% alkoxylated alcohol<br>1% olefin sulfonate |
| 35 | 0.5% alkoxylated alcohol<br>0.5% olefin sulfonate<br>0.25% carboxylate |
| 36 | 0.6% co-solvent<br>0.6% olefin sulfonate |
| 37 | 0.6% co-solvent<br>0.3% disulfonate<br>0.3% olefin sulfonate |
| 38 | 0.6% co-solvent<br>0.4% disulfonate<br>0.2% olefin sulfonate |
| 39 | 0.5% alkoxylated C6-C16 alcohol<br>0.4% disulfonate<br>0.3% olefin sulfonate |
| 40 | 0.4% alkoxylated C6-C16 alcohol<br>0.35% disulfonate<br>0.25% olefin sulfonate<br>0.5% co-solvent |
| 41 | 0.25% Guerbet alkoxylated carboxylate<br>0.5% alkoxylated C6-C16 alcohol<br>0.35% disulfonate<br>0.15% olefin sulfonate<br>0.35% co-solvent |
| 42 | 0.25% Guerbet alkoxylated carboxylate<br>0.25% alkoxylated C6-C16 alcohol<br>0.25% olefin sulfonate<br>0.25% co-solvent |
| 43 | 0.25% Guerbet alkoxylated carboxylate<br>0.25% alkoxylated C6-C16 alcohol<br>0.25% olefin sulfonate<br>0.25% alkoxylated alcohol |
| 44 | 0.25% Guerbet alkoxylated carboxylate<br>0.35% olefin sulfonate<br>0.5% alkoxylated alcohol |
| 45 | 0.25% Guerbet alkoxylated carboxylate<br>0.25% alkoxylated C6-C16 alcohol<br>0.15% olefin sulfonate<br>0.1% disulfonate<br>0.25% co-solvent |
| 46 | 0.25% Guerbet alkoxylated carboxylate<br>0.25% alkoxylated C6-C16 alcohol<br>0.25% olefin sulfonate<br>0.25% glycosides or glucosides<br>0.25% co-solvent<br>0.15% disulfonate |
| 47 | 0.25% Guerbet alkoxylated carboxylate<br>0.25% olefin sulfonate<br>0.5% glycosides or glucosides<br>0.25% co-solvent |
| 48 | 0.65% Guerbet alkoxylated carboxylate<br>0.35% olefin sulfonate<br>0.33% alkoxylated alkylphenol<br>0.5% co-solvent<br>0.25% second co-solvent |
| 49 | 0.9% Guerbet alkoxylated carboxylate<br>0.9% alkoxylated C6-C16 alcohol<br>1.2% olefin sulfonate<br>0.225% co-solvent |
| 50 | 1% alkoxylated C6-C16 alcohol<br>1% olefin sulfonate |
| 51 | 1% alkoxylated C6-C16 alcohol<br>0.75% olefin sulfonate<br>0.5% disulfonate |
| 52 | 1% alkoxylated C6-C16 alcohol<br>0.75% olefin sulfonate<br>0.3% disulfonate |
| 53 | 0.5% alkoxylated C6-C16 alcohol<br>0.85% olefin sulfonate<br>0.15% disulfonate |
| 54 | 0.9% Guerbet alkoxylated carboxylate<br>0.9% alkoxylated C6-C16 alcohol<br>1.2% olefin sulfonate<br>0.225% co-solvent |
| 55 | 1% alkoxylated C6-C16 alcohol<br>0.75% olefin sulfonate<br>0.3% disulfonate |
| 56 | 0.9% Guerbet alkoxylated carboxylate<br>0.9% alkoxylated C6-C16 alcohol<br>1.2% olefin sulfonate<br>0.225% co-solvent |
| 57 | 0.5% Guerbet alkoxylated carboxylate<br>0.5% alkoxylated C6-C16 alcohol<br>0.15% olefin sulfonate<br>0.35% disulfonate<br>0.5% alkoxylated alkylphenol<br>0.13% co-solvent |
| 58 | 0.5% Guerbet alkoxylated carboxylate<br>0.5% alkoxylated C6-C16 alcohol<br>0.5% olefin sulfonate<br>0.5% disulfonate |
| 59 | 0.5% C6-C16 alcohol alkoxylated carboxylate<br>0.25% alkoxylated C6-C16 alcohol<br>0.15% olefin sulfonate<br>0.35% disulfonate |
| 60 | 0.5% Guerbet alkoxylated carboxylate<br>0.25% C6-C16 alcohol alkoxylated carboxylate<br>0.5% alkoxylated C6-C16 alcohol<br>0.5% olefin sulfonate<br>0.1% disulfonate<br>0.5% co-solvent |
| 61 | 0.5% C6-C16 alcohol alkoxylated carboxylate<br>0.25% alkoxylated C6-C16 alcohol<br>0.15% olefin sulfonate<br>0.35% disulfonate |
| 62 | 0.5% Guerbet alkoxylated carboxylate<br>0.5% alkoxylated C6-C16 alcohol<br>0.15% olefin sulfonate<br>0.35% disulfonate<br>0.25% cetyl betaine |
| 63 | 0.5% Guerbet alkoxylated carboxylate<br>0.25% C6-C16 alcohol alkoxylated carboxylate<br>0.5% alkoxylated C6-C16 alcohol<br>0.5% olefin sulfonate<br>0.1% disulfonate<br>0.5% co-solvent<br>0.02% cetyl Betaine |
| 64 | 0.5% olefin sulfonate<br>0.5% alkyl aryl sulfonate<br>0.5% disulfonate |
| 65 | 0.5% olefin sulfonate<br>0.5% alkyl aryl sulfonate<br>0.5% disulfonate<br>2% co-solvent |
| 66 | 0.5% olefin sulfonate<br>0.5% alkyl aryl sulfonate<br>0.5% disulfonate<br>2% co-solvent |
| 67 | 0.5% olefin sulfonate<br>0.5% alkyl aryl sulfonate<br>0.5% disulfonate<br>0.5% alkoxylated C6-C16 alcohol<br>0.5% co-solvent |

-continued

| Example | Surfactants and Co-Solvents in Aqueous Composition (in weight percent) |
|---|---|
| 68 | 0.5% olefin sulfonate<br>0.5% alkyl aryl sulfonate<br>0.5% disulfonate<br>0.5% alkoxylated alkylphenol |
| 69 | 0.5% olefin sulfonate<br>0.5% alkyl aryl sulfonate<br>0.5% alkoxylated alkylphenol |

Methods of Use

Also provided are methods of using the olefin surfactants described herein in oil and gas operations. The oil and gas operation can comprise for example, an enhanced oil recovery (EOR) operation (e.g., an improved oil recovery (IOR) operation, a surfactant (S) flooding operation, an alkaline-surfactant (AS) flooding operation, a surfactant-polymer (SP) flooding operation, a alkaline-surfactant-polymer (ASP) flooding operation, a conformance control operation, or any combination thereof) a hydraulic fracturing operation, a wellbore clean-up operation, a stimulation operation, or any combination thereof. In certain examples, the surfactant compositions described herein can be used as an injection fluid, as a component of an injection fluid, as a hydraulic fracturing fluid, or as a component of a hydraulic fracturing fluid.

For example, provided herein methods of treating a subterranean formation that comprise introducing an aqueous fluid comprising water and a surfactant package through a wellbore into the subterranean formation. The surfactant package can comprise an olefin sulfonate described herein. The subterranean formation can be a subsea reservoir and/or subsurface reservoir.

In some embodiments, the compositions described herein can be used in treatment operations in an unconventional subterranean formation. For example, the aqueous compositions (injection compositions) described herein can be used as part of a completion and/or fracturing operation. Accordingly, methods of treating the subterranean formation can comprise a fracturing operation. For example, the method can comprise injecting the aqueous fluid into the subterranean formation through the wellbore at a sufficient pressure to create or extend at least one fracture in a rock matrix of the subterranean formation in fluid communication with the wellbore.

In certain embodiments, the fracturing operation can comprise combining a surfactant package described herein with one or more additional components to form an injection composition; and injecting the injection composition through a wellbore and into the unconventional subterranean formation at a sufficient pressure and at a sufficient rate to fracture the unconventional subterranean formation. In some embodiments, the wellbore is a hydraulic fracturing wellbore associated with a hydraulic fracturing well, for example, that may have a substantially vertical portion only, or a substantially vertical portion and a substantially horizontal portion below the substantially vertical portion. In some embodiments, the fracturing operation can be performed in a new well (e.g., a well that has not been previously fractured). In other embodiments, the injection composition can be used in a fracturing operation in an existing well (e.g., in a refracturing operation).

In some embodiments, the method can comprise performing a fracturing operation on a region of the unconventional subterranean formation proximate to a new wellbore. In some embodiments, the method can comprise performing a fracturing operation on a region of the unconventional subterranean formation proximate to an existing wellbore. In some embodiments, the method can comprise performing a refracturing operation on a previously fractured region of the unconventional subterranean formation proximate to a new wellbore. In some embodiments, the method can comprise performing a refracturing operation on a previously fractured region of the unconventional subterranean formation proximate to an existing wellbore. In some embodiments, the method can comprise performing a fracturing operation on a naturally fractured region of the unconventional subterranean formation proximate to a new wellbore (e.g., an infill well). In some embodiments, the method can comprise performing a fracturing operation on a naturally fractured region of the unconventional subterranean formation proximate to an existing wellbore.

In cases where the fracturing method comprises a refracturing method, the previously fractured region of the unconventional reservoir can have been fractured by any suitable type of fracturing operation. For example, the fracturing operation may include hydraulic fracturing, fracturing using electrodes such as described in U.S. Pat. Nos. 9,890,627, 9,840,898, U.S. Patent Publication No. 2018/0202273, or fracturing with any other available equipment or methodology. In some embodiments, the fracturing operation can further comprise adding a tracer to the injection composition prior to introducing the injection composition through the wellbore into the unconventional subterranean formation; recovering the tracer from the fluids produced from the unconventional subterranean formation through the wellbore, fluids recovered from a different wellbore in fluid communication with the unconventional subterranean formation, or any combination thereof; and comparing the quantity of tracer recovered from the fluids produced to the quantity of tracer introduced to the injection composition. The tracer can comprise a proppant tracer, an oil tracer, a water tracer, or any combination thereof. Example tracers are known in the art, and described, for example, in U.S. Pat. No. 9,914,872 and Ashish Kumar et al., Diagnosing Fracture-Wellbore Connectivity Using Chemical Tracer Flowback Data, URTeC 2902023, Jul. 23-25, 2018, page 1-10, Texas, USA.

The injection composition can be used at varying points throughout a fracturing operation. For example, the injection compositions described herein can be used as an injection fluid during the first, middle or last part of the fracturing process, or throughout the entire fracturing process. In some embodiments, the fracturing process can include a plurality of stages and/or sub-stages. For example, the fracturing process can involve sequential injection of fluids in different stages, with each of the stages employing a different aqueous-based injection fluid system (e.g., with varying properties such as viscosity, chemical composition, etc.). Example fracturing processes of this type are described, for example, in U.S. Patent Application Publication Nos. 2009/0044945 and 2015/0083420, each of which is hereby incorporated herein by reference in its entirely.

In these embodiments, the injection compositions described herein can be used as an injection fluid (optionally with additional components) during any or all of the stages and/or sub-stages. Stages and/or sub-stages can employ a wide variety of aqueous-based injection fluid systems, including linear gels, crosslinked gels, and friction-reduced water. Linear gel fracturing fluids are formulated with a wide array of different polymers in an aqueous base. Polymers that are commonly used to formulate these linear gels include guar, hydroxypropyl guar (HPG), carboxymethyl HPG (CMHPG), and hydroxyethyl cellulose (HEC). Crosslinked gel fracturing fluids utilize, for example, borate ions to crosslink the hydrated polymers and provide increased viscosity. The polymers most often used in these fluids are guar and HPG. The crosslink obtained by using borate is reversible and is triggered by altering the pH of the fluid system. The reversible characteristic of the crosslink in borate fluids helps them clean up more effectively, resulting in good regained permeability and conductivity. The surfactant packages described herein can be added to any of these aqueous-based injection fluid systems.

In some embodiments, the surfactant packages described herein can be combined with one or more additional components in a continuous process to form the injection compositions described herein (which is subsequently injected). In other embodiments, the surfactant package can be intermittently added to one or more additional components, thereby providing the injections compositions only during desired portions of the treatment operation (e.g., during one or more phases or stages of a fracturing operation). For example, the surfactant package could be added when injecting slickwater, when injecting fracturing fluid with proppant, during an acid wash, or during any combination thereof. In a specific embodiment, the surfactant package is continuously added to the one or more additional components after acid injection until completion of hydraulic fracturing and completion fluid flow-back. When intermittently dosed, the surfactant package can be added to the one or more additional components once an hour, once every 2 hours, once every 4 hours, once every 5 hours, once every 6 hours, twice a day, once a day, or once every other day, for example. In some embodiments when used in a fracturing operation, the injection composition can have a total surfactant concentration of from 0.01% to 1% by weight, based on the total weight of the injection composition.

In some embodiments, the injection compositions described herein can be used as part of a reservoir stimulation operation (also referred to as wellbore cleanup operations or near-wellbore cleanup operations). The stimulation operation can be performed on a conventional subterranean formation or an unconventional subterranean formation. The stimulation operation can be performed on a subterranean formation that is fractured (naturally fractured and/or previously fractured in a fracturing operation) or unfractured. The stimulation operation can be performed in a new wellbore or an existing wellbore.

In some operations, the fluid can be injected to alter the wettability of existing fractures within the formation (without further fracturing the formation significantly by either forming new fractures within the formation and/or extending the existing fractures within the formation). In such stimulation operations, no proppant is used, and fluid injection generally occurs at a lower pressure.

In some cases, the existing fractures can be naturally occurring fractures present within a formation. For example, in some embodiments, the formation can comprise naturally fractured carbonate or naturally fractured sandstone. The presence or absence of naturally occurring fractures within a subterranean formation can be assessed using standard methods known in the art, including seismic surveys, geology, outcrops, cores, logging, reservoir characterization including preparing grids, etc.

In some embodiments, methods for stimulating a subterranean formation with a fluid can comprise introducing an aqueous composition (injection composition) as described herein through a wellbore into the subterranean formation; allowing the injection composition to imbibe into a rock matrix of the subterranean formation for a period of time; and producing fluids from the subterranean formation through the wellbore. The injection fluid can comprise a surfactant package and one or more additional components as described herein. In these methods, the same wellbore can be used for both introducing the injection composition and producing fluids from the subterranean formation., the same wellbore can be used. In some embodiments, introduction of the injection composition can increase the production of hydrocarbons from the same wellbore, from a different wellbore in fluid communication with the subterranean formation, or any combination thereof.

In some embodiments, the stimulation operation can further comprise preparing the injection composition. For example, in some embodiments, the stimulation operation can further comprise combining a surfactant package described herein with one or more additional components to form an injection composition.

In some embodiments when used in a stimulation operation, the injection composition can have a total surfactant concentration of from 0.2% to 5% by weight, based on the total weight of the injection composition.

In some embodiments, introducing an injection composition as described herein through a wellbore into the subterranean formation can comprise injecting the injection composition through the wellbore and into the subterranean formation at a sufficient pressure and at a sufficient rate to stimulate hydrocarbon production from naturally occurring fractures in the subterranean formation.

The injection composition as described herein can be allowed to contact the rock matrix (e.g., to imbibe into the rock matrix) of the subterranean formation for varying periods of time depending on the nature of the rock matrix. The imbibing can occur during the introducing step, between the introducing and producing step, or any combination thereof. In some examples, the injection composition can be allowed to imbibe into the rock matrix of the subterranean formation for at least one day (e.g., at least two days, at least three days, at least four days, at least five days, at least six days, at least one week, at least two weeks, at least three weeks, at least one month, at least two months, at least three months, at least four months, or at least five months). In some examples, the injection composition can be allowed to imbibe into the rock matrix of the subterranean formation for six months or less (e.g., five months or less, four months or less, three months or less, two months or less, one month or less, three weeks or less, two weeks or less, one week or less, six days or less, five days or less, four days or less, three days or less, or two days or less).

In some embodiments, the wellbore used in the stimulation operation may have a substantially vertical portion only, or a substantially vertical portion and a substantially horizontal portion below the substantially vertical portion.

In some embodiments, the stimulation methods described herein can comprise stimulating a naturally fractured region of the subterranean formation proximate to a new wellbore (e.g., an infill well). In some embodiments, the stimulation methods described herein can comprise stimulating a naturally fractured region of the subterranean formation proximate to an existing wellbore.

In some embodiments, the stimulation methods described herein can comprise stimulating a previously fractured or previously refractured region of the subterranean formation proximate to a new wellbore (e.g., an infill well). In some embodiments, the stimulation methods described herein can comprise stimulating a previously fractured or previously refractured region of the subterranean formation proximate to an existing wellbore.

The previous refracturing operation may include hydraulic fracturing, fracturing using electrodes such as described in U.S. Pat. Nos. 9,890,627, 9,840,898, U.S. Patent Publication No. 2018/0202273, or refracturing with any other available equipment or methodology. In some embodiments, after a formation that has fractures, such as naturally occurring factures, fractures from a fracture operation, fractures from a refracturing operation, or any combination thereof, the fractured formation may be stimulated. For example, a formation may be stimulated after a sufficient amount of time has passed since the fracturing operation with electrodes or refracturing operation with electrodes occurred in that formation so that the electrical pulses utilized to fracture or refracture that formation do not substantially affect the injection composition.

In some embodiments, the stimulation operation can further comprise adding a tracer to the injection composition prior to introducing the low particle size injection fluid through the wellbore into the subterranean formation; recovering the tracer from the fluids produced from the subterranean formation through the wellbore, fluids recovered from a different wellbore in fluid communication with the subterranean formation, or any combination thereof; and comparing the quantity of tracer recovered from the fluids produced to the quantity of tracer introduced to the injection composition. The tracer can be any suitable tracer, such as a water tracer or an oil tracer.

In some embodiments, the subterranean formation can have a permeability of from 26 millidarcy to 40,000 millidarcy. In some embodiments, the methods of treating the subterranean formation can comprise an EOR operation. For example, the wellbore can comprise an injection wellbore, and the method can comprise a method for hydrocarbon recovery that comprises (a) injecting the aqueous fluid (a surfactant composition) through the injection wellbore into the subterranean formation; and (b) producing fluids from a production wellbore spaced apart from the injection wellbore a predetermined distance and in fluid communication with the subterranean formation. The injection of the aqueous fluid can increase the flow of hydrocarbons to the production well.

Also provided are methods of displacing a hydrocarbon material in contact with a solid material. These methods can include contacting a hydrocarbon material with a surfactant composition (injection composition) described herein, wherein the hydrocarbon material is in contact with a solid material. The hydrocarbon material is allowed to separate from the solid material thereby displacing the hydrocarbon material in contact with the solid material. In some embodiments, the surfactant composition can comprise a borate-acid buffer.

In other embodiments, the hydrocarbon material is unrefined petroleum (e.g., in a petroleum reservoir). In some further embodiments, the unrefined petroleum is a light oil. A "light oil" as provided herein is an unrefined petroleum with an API gravity greater than 30. In some embodiments, the API gravity of the unrefined petroleum is greater than 30. In other embodiments, the API gravity of the unrefined petroleum is greater than 40. In some embodiments, the API gravity of the unrefined petroleum is greater than 50. In other embodiments, the API gravity of the unrefined petroleum is greater than 60. In some embodiments, the API gravity of the unrefined petroleum is greater than 70. In other embodiments, the API gravity of the unrefined petroleum is greater than 80. In some embodiments, the API gravity of the unrefined petroleum is greater than 90. In other embodiments, the API gravity of the unrefined petroleum is greater than 100. In some other embodiments, the API gravity of the unrefined petroleum is between 30 and 100.

In other embodiments, the hydrocarbons or unrefined petroleum can comprise crude having an $H_2S$ concentration of at least 0.5%, a $CO_2$ concentration of 0.3%, or any combination thereof.

In some embodiments, the hydrocarbons or unrefined petroleum can comprise crude having an $H_2S$ concentration of at least 0.5% (e.g., at least 1%, at least 1.5%, at least 2%, at least 2.5%, at least 3%, at least 3.5%, at least 4%, or at least 4.5%). In some embodiments, the hydrocarbons or unrefined petroleum can comprise crude having an $H_2S$ concentration of 5% or less (4.5% or less, 4% or less, 3.5% or less, 3% or less, 2.5% or less, 2% or less, 1.5% or less, or 1% or less).

The hydrocarbons or unrefined petroleum can comprise crude having an $H_2S$ concentration ranging from any of the minimum values described above. For example, in some embodiments, the hydrocarbons or unrefined petroleum can comprise crude having an $H_2S$ concentration of from 0.5% to 5% (e.g., from 0.5% to 2.5%).

In some embodiments, the hydrocarbons or unrefined petroleum can comprise crude having a $CO_2$ concentration of at least 0.3% (e.g., at least 0.5%, at least 1%, at least 1.5%, at least 2%, at least 2.5%, at least 3%, at least 3.5%, at least 4%, or at least 4.5%). In some embodiments, the hydrocarbons or unrefined petroleum can comprise crude having a $CO_2$ concentration of 5% or less (4.5% or less, 4% or less, 3.5% or less, 3% or less, 2.5% or less, 2% or less, 1.5% or less, 1% or less, or 0.5% or less).

The hydrocarbons or unrefined petroleum can comprise crude having a $CO_2$ concentration ranging from any of the minimum values described above. For example, in some embodiments, the hydrocarbons or unrefined petroleum can comprise crude having a $CO_2$ concentration of from 0.3% to 5% (e.g., from 0.3% to 2.5%).

The solid material may be a natural solid material (i.e., a solid found in nature such as rock). The natural solid material may be found in a petroleum reservoir. In some embodiments, the method is an enhanced oil recovery method. Enhanced oil recovery methods are well known in the art. A general treatise on enhanced oil recovery methods is Basic Concepts in Enhanced Oil Recovery Processes edited by M. Baviere (published for SCI by Elsevier Applied Science, London and New York, 1991). For example, in an enhanced oil recovery method, the displacing of the unrefined petroleum in contact with the solid material is accomplished by contacting the unrefined with a surfactant composition provided herein, wherein the unrefined petroleum is in contact with the solid material. The unrefined petroleum may be in an oil reservoir. The composition can be pumped into the reservoir in accordance with known enhanced oil recovery parameters. Upon contacting the unrefined petroleum, the aqueous composition can form an emulsion composition with the unrefined petroleum.

In some embodiments, the natural solid material can be rock or regolith. The natural solid material can be a geological formation such as clastics or carbonates. The natural solid material can be either consolidated or unconsolidated material or mixtures thereof. The hydrocarbon material may be trapped or confined by "bedrock" above or below the natural solid material. The hydrocarbon material may be found in fractured bedrock or porous natural solid material.

In other embodiments, the regolith is soil. In other embodiments, the solid material can be, for example, oil sand or tar sands.

In other embodiments, the solid material can comprise equipment associated with an oil and gas operation. For example, the solid material can comprise surface processing equipment, downhole equipment, pipelines and associated equipment, pumps, and other equipment which contacts hydrocarbons during the course of an oil and gas operation.

Surfactant packages as described herein (as well as the resulting surfactant compositions) can be optimized for each formation and/or for the desired oil and gas operation. For example, a surfactant package can be tested at a specific reservoir temperature and salinity, and with specific additional components. Actual native reservoir fluids may also be used to test the compositions.

In some embodiments, the subterranean formation can have a temperature of at least 75° F. (e.g., at least 80° F., at least 85° F., at least 90° F., at least 95° F., at least 100°, at least 105° F., at least 110° F., at least 115° F., at least 120° F., at least 125° F., at least 130° F., at least 135° F., at least 140° F., at least 145° F., at least 150° F., at least 155° F., at least 160° F., at least 165° F., at least 170° F., at least 175° F., at least 180° F., at least 190° F., at least 200° F., at least 205° F., at least 210° F., at least 215° F., at least 220° F., at least 225° F., at least 230° F., at least 235° F., at least 240° F., at least 245° F., at least 250° F., at least 255° F., at least 260° F., at least 265° F., at least 270° F., at least 275° F., at least 280° F., at least 285° F., at least 290° F., at least 295° F., at least 300° F., at least 305° F., at least 310° F., at least 315° F., at least 320° F., at least 325° F., at least 330° F., at least 335° F., at least 340° F., or at least 345° F.). In some embodiments, the subterranean formation can have a temperature of 350° F. or less (e.g., 345° F. or less, 340° F. or less, 335° F. or less, 330° F. or less, 325° F. or less, 320° F. or less, 315° F. or less, 310° F. or less, 305° F. or less, 300° F. or less, 295° F. or less, 290° F. or less, 285° F. or less, 280° F. or less, 275° F. or less, 270° F. or less, 265° F. or less, 260° F. or less, 255° F. or less, 250° F. or less, 245° F. or less, 240° F. or less, 235° F. or less, 230° F. or less, 225° F. or less, 220° F. or less, 215° F. or less, 210° F. or less, 205° F. or less, 200° F. or less, 195° F. or less, 190° F. or less, 185° F. or less, 180° F. or less, 175° F. or less, 170° F. or less, 165° F. or less, 160° F. or less, 155° F. or less, 150° F. or less, 145° F. or less, 140° F. or less, 135° F. or less, 130° F. or less, 125° F. or less, 120° F. or less, 115° F. or less, 110° F. or less, 105° F. or less, 100° F. or less, 95° F. or less, 90° F. or less, 85° F. or less, or 80° F. or less).

The subterranean formation can have a temperature ranging from any of the minimum values described above to any of the maximum values described above. For example, in some embodiments, the subterranean formation can have a temperature of from 75° F. to 350° F. (approximately 24° C. to 176° C.), from 150° F. to 250° F. (approximately 66° C. to 121° C.), from 110° F. to 350° F. (approximately 43° C. to 176° C.), from 110° F. to 150° F. (approximately 43° C. to 66° C.), from 150° F. to 200° F. (approximately 66° C. to 93° C.), from 200° F. to 250° F. (approximately 93° C. to 121° C.), from 250° F. to 300° F. (approximately 121° C. to 149° C.), from 300° F. to 350° F. (approximately 149° C. to 176° C.), from 110° F. to 240° F. (approximately 43° C. to 116° C.), or from 240° F. to 350° F. (approximately 116° C. to 176° C.).

In some embodiments, the salinity of subterranean formation can be at least 5,000 ppm TDS (e.g., at least 25,000 ppm TDS, at least 50,000 ppm TDS, at least 75,000 ppm TDS, at least 100,000 ppm TDS, at least 125,000 ppm TDS, at least 150,000 ppm TDS, at least 175,000 ppm TDS, at least 200,000 ppm TDS, at least 225,000 ppm TDS, at least 250,000 ppm TDS, or at least 275,000 ppm TDS). In some embodiments, the salinity of subterranean formation can be 300,000 ppm TDS or less (e.g., 275,000 ppm TDS or less, 250,000 ppm TDS or less, 225,000 ppm TDS or less, 200,000 ppm TDS or less, 175,000 ppm TDS or less, 150,000 ppm TDS or less, 125,000 ppm TDS or less, 100,000 ppm TDS or less, 75,000 ppm TDS or less, 50,000 ppm TDS or less, or 25,000 ppm TDS or less).

The salinity of subterranean formation can range from any of the minimum values described above to any of the maximum values described above. For example, in some embodiments, the salinity of subterranean formation can be from 5,000 ppm TDS to 300,000 ppm TDS (e.g., from 100,000 ppm to 300,000 ppm TDS).

In some embodiments, the subterranean formation can be oil-wet. In some embodiments, the subterranean formation can be water-wet. In some embodiments, the subterranean formation can be mixed-wet. In some embodiments, the subterranean formation can be intermediate-wet.

In some embodiments, the injection composition described herein can be introduced at a wellhead pressure of at least 0 PSI (e.g., at least 1,000 PSI, at least 2,000 PSI, at least 3,000 PSI, at least 4,000 PSI, at least 5,000 PSI, at least 6,000 PSI, at least 7,000 PSI, at least 8,000 PSI, at least 9,000 PSI, at least 10,000 PSI, at least 15,000 PSI, at least 20,000 PSI, or at least 25,000 PSI). In some embodiments, the injection composition can be introduced at a wellhead pressure of 30,000 PSI or less (e.g., 25,000 PSI or less, 20,000 PSI or less, 15,000 PSI or less, 10,000 PSI or less, 9,000 PSI or less, 8,000 PSI or less, 7,000 PSI or less, 6,000 PSI or less, 5,000 PSI or less, 4,000 PSI or less, 3,000 PSI or less, 2,000 PSI or less, or 1,000 PSI or less).

The injection composition (surfactant composition) described herein can be introduced at a wellhead pressure ranging from any of the minimum values described above to any of the maximum values described above. For example, in some embodiments, the injection composition can be introduced at a wellhead pressure of from 0 PSI to 30,000 PSI (e.g., from 6,000 PSI to 30,000 PSI, or from 5,000 PSI to 10,000 PSI. In some embodiments, the injection composition can be used in a reservoir stimulation operation, and the injection composition can be introduced at a wellhead pressure of from 0 PSI to 1,000 PSI.

In some embodiments, there is no need to drill the wellbore. In some embodiments, the wellbore has been drilled and completed, and hydrocarbon production has occurred from the wellbore. In other embodiments, methods described herein can optionally include one or more of drilling the wellbore, completing the wellbore, and producing hydrocarbons from the wellbore (prior to injection of the surfactant composition).

A number of embodiments of the disclosure have been described. Nevertheless, it will be understood that various modifications may be made without departing from the spirit and scope of the invention. Accordingly, other embodiments are within the scope of the following claims.

EXAMPLES

By way of non-limiting illustration, examples of certain embodiments of the present disclosure are given below.

Example 1. Dimerization of Propylene Oligomer

F-24X clay catalyst (628 g, 15 wt %) was added to a solution of propylene tetramer ($PP_4$) (4186 g) in a 10 L round bottom flask equipped with an overhead stirrer and reflux condenser. The reaction mixture was blanketed with nitrogen and heated to 100° C. for 138 h. The reaction mixture was filtered, and the unreacted propylene tetramer was removed by distillation to afford 1339 g of propylene tetramer dimer $(PP_4)_2$.

Example 2. Preparation of an Olefin Sulfonate

Propylene tetramer ($PP_4$) was sulfonated in a stainless steel, water jacketed, falling film tubular reactor (about 0.19" ID×60" length) using $SO_3$/air under the following conditions:
Propylene oligomer feed temperature=30° C.
Reactor temperature=50° C.
Air flow=195 L/h
Makeup air flow=11 L/h
$SO_2$ flow=16 L/h
$SO_2$ to $SO_3$ conversion=87%
Propylene oligomer feed rate=1.73 g/min
CMR ($SO_3$/feed)=1.05

The reaction generates several products including olefin sulfonic acid, sulfuric acid, and sultone. In this example, the resulting product had the following properties: 5.87 wt % $H_2SO_4$ and 33.3 wt % olefin sulfonic acid. The olefin sulfonic acid can be detected by cyclohexylamine titration.

The olefin sulfonic acid (30 g) was then neutralized by addition of a 50 wt % aqueous NaOH solution (3.8 g) in portions between 25° C. and 51° C. over 30 minutes with stirring. The pH of the neutralized olefin sulfonate was 12.7 (about 1 wt % in water solution). The ESI mass spectrum showed a major constituent in the sodium sulfonate composition to have a m/z charge ratio of 247.13 corresponding to a $[C_{12}H_{23}O_3S]^-$ species (FIG. 1).

Example 3. Preparation of an Olefin Sulfonate

Propylene pentamer ($PP_5$) was sulfonated in a stainless steel, water jacketed, falling film tubular reactor (about 0.19" ID×60" length) using $SO_3$/air under the following conditions:
Propylene oligomer feed temperature=30° C.
Reactor temperature=40° C.
Air flow=195 L/h
Makeup air flow=11 L/h
$SO_2$ flow=16 L/h
$SO_2$ to $SO_3$ conversion=87%
Propylene oligomer feed rate=2.17 g/min
CMR ($SO_3$/feed)=1.00

The resulting product had the following properties: 3.22 wt % $H_2SO_4$ and 34.1 wt % olefin sulfonic acid (cyclohexylamine titration).

Figure 2:
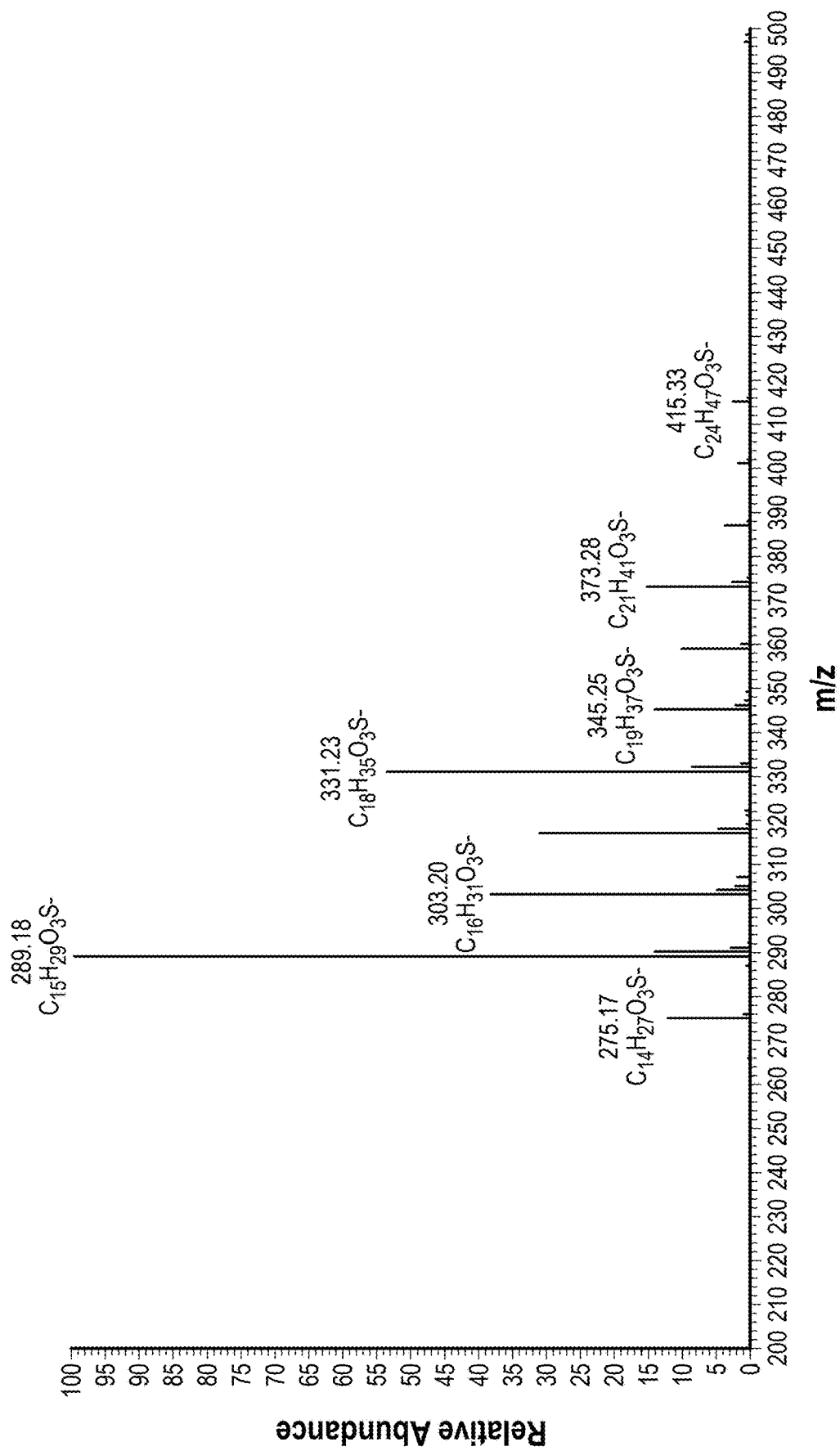
FIG. 2 is a mass spectrum of an internal olefin sulfonate sample as described in Example 3.

The olefin sulfonic acid (177 g) was then neutralized by addition of a 50 wt % aqueous NaOH solution (23.6 g) in portions between 25° C. and 51° C. over 30 minutes with stirring. The pH of the neutralized olefin sulfonate was 11.1 (about 1 wt % in water solution). The ESI mass spectrum showed a major constituent in the sodium sulfonate composition to have a m/z charge ratio of 289.18 (FIG. 2) corresponding to $[C_{15}H_{29}SO_3]^-$ species.

Example 4. Preparation of Olefin Sulfonate

Propylene tetramer dimer $(PP_4)_2$ was sulfonated in a stainless steel, water jacketed, falling film tubular reactor (about 0.19" ID×60" length) using $SO_3$/air under the following conditions:
Propylene oligomer feed temperature=30° C.
Reactor temperature=40° C.
Air flow=195 L/h
Makeup air flow=11 L/h
$SO_2$ flow=16 L/h
$SO_2$ to $SO_3$ conversion=87%
Propylene oligomer feed rate=3.52 g/min
CMR ($SO_3$/feed)=1.00

The resulting product had the following properties: 6.22 wt % $H_2SO_4$ and 19.6 wt % olefin sulfonic acid (cyclohexylamine titration).

Figure 3:
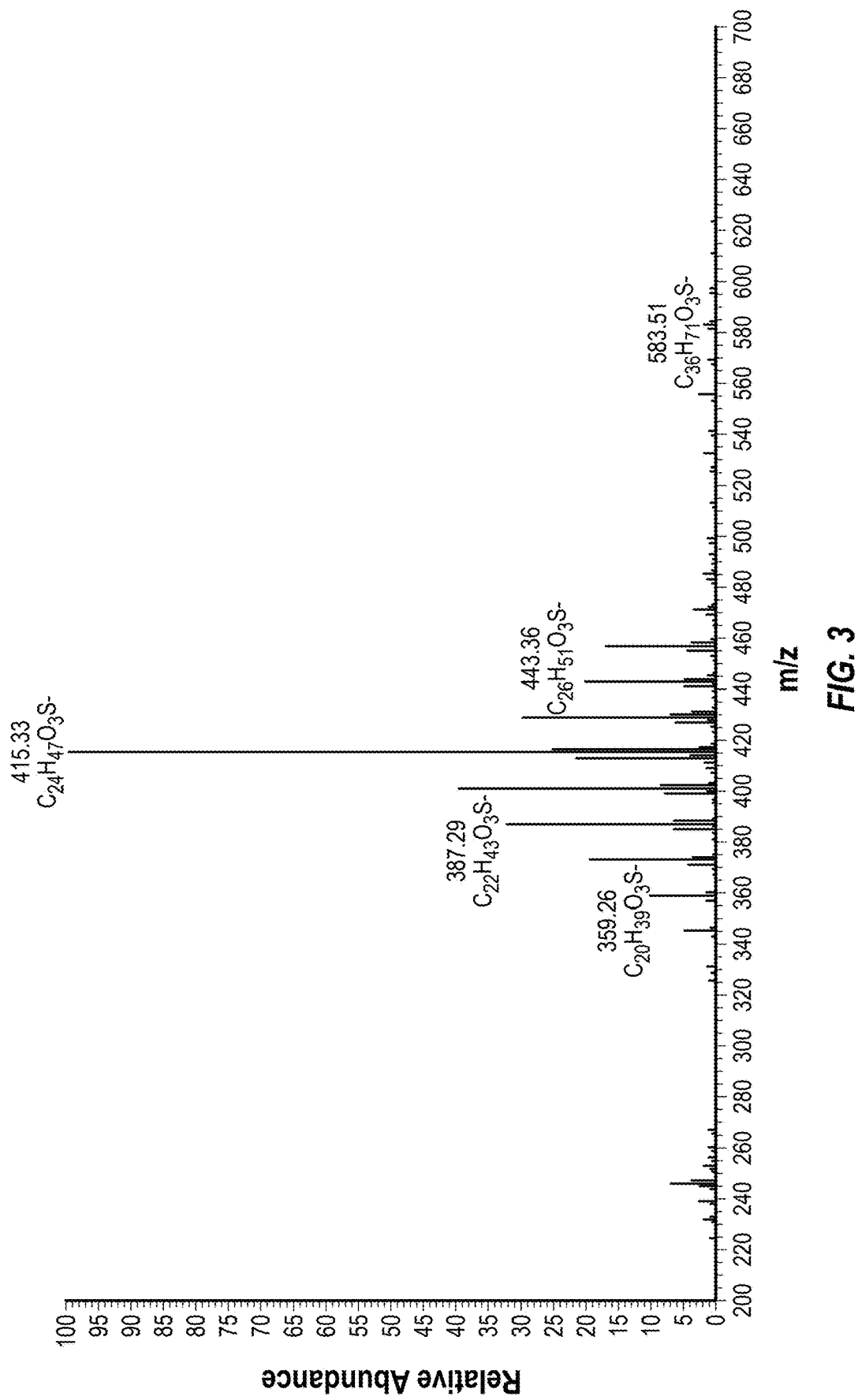
FIG. 3 is a mass spectrum of an internal olefin sulfonate sample as described in Example 4.

The olefin sulfonic acid (145 g) was then neutralized by addition of a 50 wt. % aqueous NaOH solution (18.5 g) in portions between 25° C. and 51° C. over 30 minutes with stirring. The pH of the neutralized olefin sulfonate was 9.6 (about 1 wt % in water solution). The ESI mass spectrum showed a major constituent in the sodium sulfonate composition to have a m/z charge ratio of 415.32 (FIG. 3) corresponding to a $[C_{24}H_{47}SO_3]^-$ species.

Example 5. Preparation of an Olefin Sulfonate

A distilled propylene oligomer fraction comprising of alkyl chain lengths of $C_{14}$-$C_{32}$ was sulfonated in a stainless steel, water jacketed, falling film tubular reactor (about 0.19" ID×60" length) using $SO_3$/air under the following conditions:
Propylene oligomer feed temperature=30° C.
Reactor temperature=40° C.
Air flow=200 L/h
Makeup air flow=11 L/h
$SO_2$ flow=16 L/h
$SO_2$ to $SO_3$ conversion=87%
Propylene oligomer feed rate=2.9 g/min The resulting sulfonic acid had the following properties: 4.28 wt % $H_2SO_4$ and 35.18 wt % sulfonic acid (cyclohexylamine titration). The sulfonic acid was digested at 65° C. for 30 minutes to afford a digested sulfonic acid with the following properties: 3.99 wt % $H_2SO_4$ and 30.03 wt % sulfonic acid.

Figure 4:
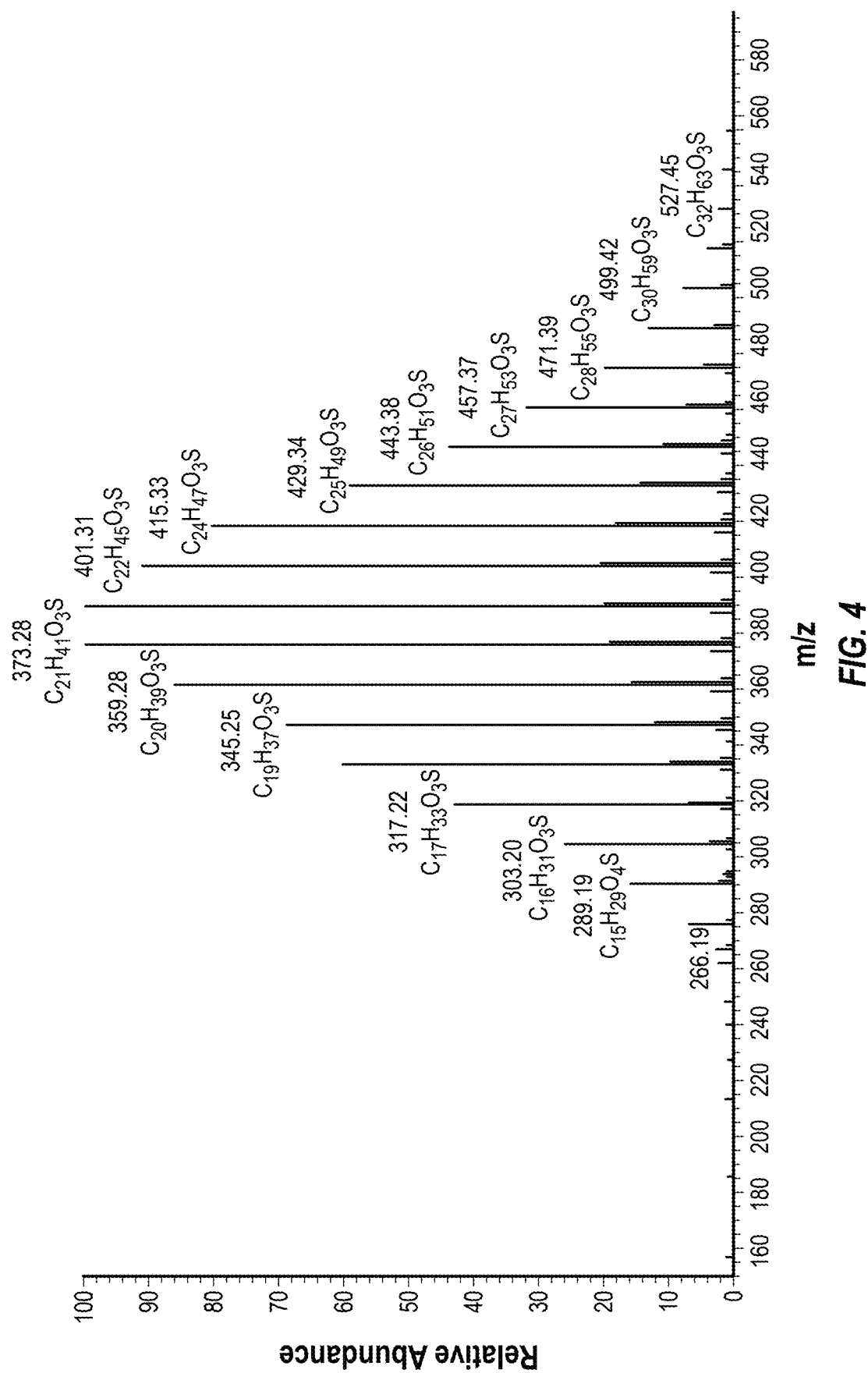
FIG. 4 is a mass spectrum of an internal olefin sulfonate sample as described in Example 5.

The digested sulfonic acid (222.3 g) was neutralized by addition of a 50 wt % aqueous NaOH solution (33.2 g) in portions between 25° C. and 51° C. over 30 minutes with stirring. The resulting sodium sulfonate was found to be 35.4 wt % active by Hyamine titration, pH=10.4 (about 1 wt. % in water solution). The ESI mass spectrum showed the major constituent in the sodium sulfonate composition to have a m/z charge ratio of 373 (see FIG. 4).

Example 6

This comparative example was obtained from conventional isomerization of normal alpha olefins and subsequent sulfonation. The resulting product is an isomerized Cao-28 alpha olefin sulfonate.

Example 7

This comparative example was obtained from conventional isomerization of normal alpha olefins and subsequent sulfonation. The resulting product is an isomerized $C_{16-18}$ alpha olefin sulfonate.

Example 8

A crude oil with a viscosity of 6 centipoise at 85 centigrade (waxy solid at room temperature) was used as base crude oil for phase behavior experiments. Phase behavior experiments can be used to understand surfactant behavior in reservoirs ("Identification and Evaluation of High-Performance EOR Surfactants." D. B. Levitt, A. C. Jackson, C. Heinson, L. N. Britton, T. Malik, V. Dwarakanath, and G. A. Pope, SPE/DOE Symposium on Improved Oil Recovery (SPE 100089), 22-26 Apr. 2006, Tulsa. Okla., USA, 2006). The phase behavior was scanned using $Na_2CO_3$ and a base brine that includes 5000 ppm NaCl in DI water.

Table 1 below summarizes how Examples 3, 4, and 5 were formulated for the measurements summarized in Table 2. Table 2 summarizes the results of optimal salinity (S*), solubility parameter (SP), interfacial tension (IFT) and aqueous stability measured against a brine gradient. All samples were equilibrated without a viscous phase. Example 3 shows higher optimal salinity (S*), and Example 4s and 5 shows a nearly equivalent solubility parameter (SP) or interfacial tension (IFT) compared to comparative Example 6.

Table 3 below summarizes how Examples 3, 4, and 5 were formulated for the measurements summarized in Table 4. All samples were equilibrated without a viscous phase. Example 3 shows higher optimal salinity (S*) and aqueous stability compared to comparative Example 6. Example 4 shows a higher solubility parameter (SP) or lower interfacial tension (IFT) compared to comparative example 6. Example 5 shows a nearly equivalent solubility parameter and identical aqueous stability compared to comparative Example 6.

All formulations gave interfacial tension (IFT) between the oil and water phase less than about 0.01 dyne/cm Table 5 summarizes the degree of branching as determined by $^1H$ NMR analysis. As shown, the internal olefin sulfonates of the present invention all show significantly higher degree of branching when compared to the comparative examples.

TABLE 1

| Component | wt % actives |
| --- | --- |
| Internal olefin sulfonate (examples 3-6) | 0.15-0.5 |
| $C_{28}$—$PO_{35}$—$EO_{10}$—$CH_2CO_2Na$ | 0.5 |
| $C_{10-30+}$ alkylated o-xylene sodium sulfonate | 0.25 |
| EGBE | 3 |

TABLE 2

| Example | S* (TDS ppm) | SP | IFT (dyne/cm) | Aqueous stability (TDS ppm) |
| --- | --- | --- | --- | --- |
| 0.25 wt % Example 3 - ($PP_5$) | 22,000 | 6 | 0.0083 | 23,000 |
| 0.15 wt % Example 4 - ($PP_4$)$_2$ | 7,500 | 11.5 | 0.0023 | 8,000 |
| 0.2 wt % Example 5 ($C_{14-32}$) | 11,000 | 11 | 0.0025 | 15,500 |
| 0.5 wt % Example 6 - Comparative $C_{20-28}$ | 15,000 | 12 | 0.0020 | 24,000 |

TABLE 3

| Component | wt % actives |
| --- | --- |
| Internal olefin sulfonate (examples 3-6) | 0.15-0.5 |
| $C_{10-30+}$ alkylated o-xylene sodium sulfonate | 1.5 |
| EGBE | 3 |

TABLE 4

| Example | S* (TDS ppm) | SP | IFT (dyne/cm) | Aqueous stability (TDS ppm) |
| --- | --- | --- | --- | --- |
| 0.25 wt % Example 3 - ($PP_5$) | 14,000 | 6 | 0.0083 | 14,000 |
| 0.15 wt % Example 4 - ($PP_4$)$_2$ | 8,000 | 8 | 0.0046 | 9,000 |
| 0.2 wt % Example 5 ($C_{14-32}$) | 9,000 | 7 | 0.006 | 13,000 |
| 0.5 wt % Example 6 - Comparative $C_{20-28}$ | 10,400 | 7.5 | 0.0053 | 13,000 |

TABLE 5

| Example | Aliphatic branching | Olefinic branching | Total branching | Average carbon atoms per chain |
| --- | --- | --- | --- | --- |
| Example 2 - ($PP_4$) | 2.82 | 1.01 | 3.83 | 14.2 |
| Example 3 - ($PP_5$) | 3.89 | 1.05 | 4.94 | 17.8 |
| Example 4 - ($PP_4$)$_2$ | 6.12 | 1.47 | 7.59 | 24.5 |
| Example 5 - $C_{14-32}$ | 1.26 | 6.90 | 8.16 | 26.6 |
| Example 6 - Comparative $C_{20-28}$ | 1.41 | 0.71 | 2.12 | 23.5 |
| Example 7 - Comparative $C_{16-18}$ | 0.10 | 0.59 | 0.69 | 16.9 |

The invention claimed is:

1. A surfactant composition comprising: an olefin sulfonate, wherein the olefin sulfonate is a propylene oligomer comprising one or more sulfonate groups and wherein the propylene oligomer has an average total branching of about 3 to about 15 per molecule.

2. The surfactant composition of claim 1, wherein the propylene oligomer is a propylene tetramer, a propylene pentamer, a dimer of propylene tetramer, a dimer of a propylene pentamer, or any combination thereof.

3. The surfactant composition of claim 1, wherein the propylene oligomer has an average carbon number of from 9 to 50.

4. The surfactant composition of claim 1, wherein the propylene oligomer has an average carbon number of from 31 to 50.

5. The surfactant composition of claim 1, wherein the average total branching is from about 3 to about 10.

6. The surfactant composition of claim 1, wherein the composition further comprises water, a co-solvent, a base, or any combination thereof.

7. The surfactant composition of claim 6, wherein the co-solvent comprises an alkanol ether, glycol ether, ethylene glycol monobutyl ether (EGBE), triethylene glycol butyl ether (TGBE), or any combination thereof.

8. The surfactant composition of claim 6, wherein the base comprises NaOH, KOH, or any combination thereof.

9. The surfactant composition of claim 1, wherein the composition further comprises an unreacted starting material for synthesis of the olefin sulfonate, a byproduct remaining from synthesis of the olefin sulfonate, or any combination thereof.

10. The surfactant composition of claim 1, wherein the average total branching number is a sum of average total aliphatic branching and average total olefinic branching as determined by NMR.

11. A concentrated surfactant composition comprising:
an olefin sulfonate, wherein the olefin sulfonate is a propylene oligomer comprising one or more sulfonate groups, the propylene oligomer having an average total branching of about 3 to about 15, and wherein the olefin sulfonate is present in about 10 wt % to about 95 wt %, based on the total weight of the concentrated surfactant composition.

* * * * *